United States Patent
Nguyen et al.

(10) Patent No.: US 11,795,450 B2
(45) Date of Patent: Oct. 24, 2023

(54) ARRAY-BASED ENZYMATIC OLIGONUCLEOTIDE SYNTHESIS

(71) Applicant: MICROSOFT TECHNOLOGY LICENSING, LLC, Redmond, WA (US)

(72) Inventors: Bichlien Nguyen, Seattle, WA (US); Sergey Yekhanin, Redmond, WA (US); Karin Strauss, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 338 days.

(21) Appl. No.: 16/563,797

(22) Filed: Sep. 6, 2019

(65) Prior Publication Data

US 2021/0071170 A1  Mar. 11, 2021

(51) Int. Cl.
| | | |
|---|---|---|
| *C12N 15/10* | (2006.01) | |
| *G16B 30/00* | (2019.01) | |
| *G16B 50/00* | (2019.01) | |
| *C12Q 1/6806* | (2018.01) | |

(52) U.S. Cl.
CPC ....... *C12N 15/1068* (2013.01); *C12Q 1/6806* (2013.01); *G16B 30/00* (2019.02); *G16B 50/00* (2019.02)

(58) Field of Classification Search
CPC ............ C12Q 1/6806; C12Q 2521/131; C12Q 2525/186; C12Q 2537/143; C12Q 2537/149; C12Q 2565/519; C12P 19/34
See application file for complete search history.

(56) References Cited

U.S. PATENT DOCUMENTS

| | | | |
|---|---|---|---|
| 6,051,380 A | 4/2000 | Sosnowski et al. | |
| 6,444,111 B1 | 9/2002 | Montgomery | |
| 8,323,939 B2 | 12/2012 | Hanzel et al. | |
| 10,289,801 B2 | 5/2019 | Church | |
| 10,435,676 B2 | 10/2019 | Champion et al. | |
| 10,683,536 B2 | 6/2020 | Efcavitch | |
| 2004/0238369 A1 | 12/2004 | Southern et al. | |
| 2006/0046262 A1 | 3/2006 | Mauritz | |
| 2007/0254327 A1 | 11/2007 | Ignatov et al. | |
| 2008/0070803 A1 | 3/2008 | Egeland | |
| 2012/0029056 A1 | 2/2012 | Alevizos et al. | |
| 2015/0196917 A1 | 7/2015 | Kay et al. | |
| 2015/0203887 A1* | 7/2015 | Lazinski et al. | C12Q 1/6855 536/24.33 |
| 2018/0267032 A1 | 9/2018 | Maurer et al. | |
| 2018/0274001 A1* | 9/2018 | Efcavitch et al. | C12P 19/34 |
| 2019/0323050 A1 | 10/2019 | Griswold et al. | |
| 2019/0360013 A1 | 11/2019 | Griswold et al. | |
| 2020/0263152 A1 | 8/2020 | Magyar et al. | |
| 2020/0362394 A1* | 11/2020 | Gawad et al. | C40B 40/06 |
| 2020/0384434 A1 | 12/2020 | Nguyen et al. | |
| 2021/0047669 A1 | 2/2021 | Nguyen | |
| 2021/0371891 A1 | 12/2021 | Nguyen et al. | |
| 2022/0136021 A1 | 5/2022 | Nguyen et al. | |
| 2022/0362734 A1 | 11/2022 | Nguyen et al. | |

FOREIGN PATENT DOCUMENTS

| | | |
|---|---|---|
| EP | 1629884 A1 | 3/2006 |
| WO | 2017142913 A1 | 8/2017 |
| WO | 2017156218 A1 | 9/2017 |
| WO | 2017176541 A1 | 10/2017 |
| WO | 2017196783 A1 | 11/2017 |
| WO | 2017223517 A1 | 12/2017 |
| WO | 2018119253 A1 | 6/2018 |
| WO | 2019079802 A1 | 4/2019 |
| WO | 2019222612 A1 | 11/2019 |
| WO | 2021034375 A1 | 2/2021 |

OTHER PUBLICATIONS

Vörtler et al. "tRNA-nucleotidyltransferases: Highly unusual RNA polymerases with vital functions" FEBS Letters vol. 584, Iss 2, Jan. 21, 2010, pp. 297-302 (Year: 2010).*
Hoang et al. "Modification of 3' Terminal Ends of DNA and RNA Using DNA Polymerase θ Terminal Transferase Activity" bio-protocol vol. 7, Iss 12, pp. 1-9, Jun. 20, 2017; DOI:10.21769/BioProtoc.2330 (Year: 2017).*
Thomas et al. "One-step enzymatic modification of RNA 3' termini using polymerase θ" Nucl. Acids Res. Vol. 47, No. 7, pp. 3272-3283, published online Mar. 1, 2019; doi: 10.1093/nar/gkz029 (Year: 2019).*
Romero, et al., "Organic Photoredox Catalysis", In Journal of Chemical Reviews, vol. 116, Issue 17, Sep. 14, 2016, pp. 10075-10166.

(Continued)

*Primary Examiner* — Kaijiang Zhang
(74) *Attorney, Agent, or Firm* — Benjamin Keim; Newport IP, LLC

(57) ABSTRACT

Array-based enzymatic oligonucleotide synthesis creates a large number of polynucleotides using an uncontrolled and template independent polymerase such as terminal deoxynucleotidyl transferase (TdT). Spatial control of reaction conditions on the surface of the array allows creation of polynucleotides with a variety of arbitrary sequences. Spatial control may be implemented by removing protecting groups attached to nucleotides only at a selected location on the array or by other techniques such as location-specific regulation of enzymatic activity. The ratio of polynucleotides with protecting groups to unprotected polynucleotides used during a cycle of synthesis is adjusted to control the length of homopolymers created by the polymerase. Digital information may be encoded in the enzymatically synthesized polynucleotides. An encoding scheme for representing digital information in a nucleotide sequence accounts for homopolymers in the polynucleotides by collapsing homopolymer strings in the sequence data to a single nucleotide or to a shorter homopolymer.

15 Claims, 6 Drawing Sheets

Specification includes a Sequence Listing.

(56) References Cited

OTHER PUBLICATIONS

Shi, et al., "Long-Lived Photoacid Based upon a Photochromic Reaction", In Journal of the American Chemical Society, vol. 133, Issue 37, Sep. 21, 2011, pp. 14699-14703.
Waters, et al., "Effect of Chelation on Iron-Chromium Redox Flow Batteries", In Journal of ACS Energy Letters, vol. 5, Issue 6, Apr. 30, 2020, pp. 1758-1762.
Yoshida, et al., "Effects of metal chelating agents on the oxidation of lipids induced by copper and iron", In Journal of Biochimica et Biophysica Acta (BBA)-Lipids and Lipid Metabolism vol. 1210, Issue 1, Dec. 2, 1993, pp. 81-88.
Dao, et al., "Photo-induced crosslinking of water-soluble polymers with a new photobase generator", In Journal of Polymer, vol. 51, No. 18, Aug. 19, 2010, pp. 4058-4062.
Liang, W., "Encapsulation of ATP into liposomes by different methods: optimization of the procedure", In Journal of Microencapsulation, vol. 21, Issue 3, May 1, 2004, pp. 251-261.
Chen, et al., "The History and Advances of Reversible Terminators Used in New Generations of Sequencing Technology", Published in Journal of Genomics, Proteomics & Bioinformatics, vol. 11, Issue 1, Feb. 2013, pp. 34-40.
Chiesi, et al., "The Use of Quench Reagents for Resolution of Single Transport Cycles in Sarcoplasmic Reticulum", Published in the Journal of Biological Chemistry, vol. 254, Issue 20, Oct. 25, 1979, pp. 10370-10377.
Lee, et al., "Photon-directed Multiplexed Enzymatic DNA Synthesis for Molecular Digital Data Storage", In repository of bioRxiv, https://doi.org/10.1101/2020.02.19.956888, Feb. 20, 2020, pp. 1-24.
Mukai, et al., "Sequential Reactions of Surface-Tethered Glycolytic Enzymes", Published in Journal of Chemistry & Biology, vol. 16, Issue 9, Sep. 25, 2009, pp. 1013-1020.
Yates, et al., "Methodologies for "Wiring" Redox Proteins/Enzymes to Electrode Surfaces", Published in Chemistry European Journal, vol. 24, Issue 47, Aug. 22, 2018, pp. 12164-12182.
Williams, et al., "An Artificial Processivity Clamp Made with Streptavidin Facilitates Oriented Attachment of Polymerase-DNA Complexes to Surfaces", Published in Journal Nucleic Acids Research, vol. 36, Issue 18, Aug. 22, 2008, pp. 1-11.
Zou, et al., "Investigating the Effect of Two-Point Surface Attachment on Enzyme Stability and Activity" In Journal of the American Chemical Society vol. 140, Issue 48, Nov. 7, 2018, pp. 16560-16569.
Nguyen, et al., "Microelectrode Arrays: A General Strategy for Using Oxidation Reactions To Site Selectively Modify Electrode Surfaces", In Journal of Langmuir vol. 30, Issue 8, Feb. 5, 2014, pp. 2280-2286.
"International Search Report and Written Opinion Issued in PCT Application No. PCT/US2020/029180", dated Jul. 16, 2020, 10 Pages.
Bi, et al., "Building Addressable Libraries: The Use of "Safety-Catch" Linkers on Microelectrode Arrays", In Journal of the American Chemical Society vol. 132, Issue 49, Nov. 19, 2010, pp. 17405-17407.
Egeland, et al., "Electrochemically Directed Synthesis of Oligonucleotides for DNA Microarray Fabrication", Published in Nucleic Acids Research, vol. 33, Issue 14, Aug. 5, 2005, pp. 1-7.
Lee, et al., "Terminator-free Template-independent Enzymatic DNA Synthesis for Digital Information Storage", Published in Nature Communications, vol. 10, Article No. 2383, Jun. 3, 2019, pp. 1-12.
Motea, et al., "Terminal Deoxynucleotidyl Transferase: The Story of a Misguided DNA Polymerase", Published in Biochimica et Biophysica Acta (BBA)—Proteins and Proteomics, vol. 1804, Issue 5, May 2010, pp. 1151-1166.
Palluk, et al., "De novo DNA Synthesis Using Polymerasenucleotide Conjugates", Published in Nature Biotechnology vol. 36, Issue 7, Jul. 2018, 24 Pages.
Zheng, et al., "A Redox-Sensitive Resin Linker for the Solid Phase Synthesis of C-Terminal Modified Peptides", In the Journal of Organic Chemistry, vol. 64, Dec. 9, 1998, Issue 1, pp. 156-161.

Devor, et al., "Strategies for Attaching Oligonucleotides to Solid Supports", Integrated DNA Technologies v6, 2014, pp. 1-22.
Hart, et al., "Synthesis and Characterization of trans-Dichlorotetrakis (imidazole)cobalt(III) Chloride: A New Cobalt(III) Coordination Complex with Potential Prodrug Properties", In Journal Bioinorganic Chemistry and Applications, vol. 2018, Article ID 4560757, Sep. 3, 2018, 7 Pages.
Heffern, et al., "Cobalt Derivatives as Promising Therapeutic Agents", In Journal Current opinion in chemical biology, vol. 17, Issue 2, 2013, pp. 189-196.
Rothstein, et al., "Solid-Phase Supports for Oligo Synthesis", Retrieved from: https://www.genengnews.com/magazine/181/solid-phase-supports-for-oligo-synthesis/4096/, Retrieved Date: Jun. 20, 2019, 08 Pages.
Sonawane, et al., "Surface Modification Chemistries of Materials Used in Diagnostic Platforms with Biomolecules", In Journal of Chemistry, vol. 2016, Article ID 9241378, May 25, 2016, pp. 1-19.
Zhang, et al., "DNA Molecules Site-Specific Immobilization and their Applications", In Central European Journal of Chemistry, vol. 12, Issue 10, Oct. 1, 2014, pp. 977-993.
Richey, et al., "Mg Anode Corrosion in Aqueous Electrolytes and Implications for Mg-Air Batteries", In Journal of The Electrochemical Society, vol. 163, Issue 6, 2016, pp. A958-A963.
Shaw, et al., "Photoredox Catalysis in Organic Chemistry", In the Journal of Organic Chemistry, vol. 81, Issue 16, Aug. 1, 2016, pp. 6898-6926.
Kosuri, et al., "Large-Scale de Novo DNA Synthesis: Technologies and Applications", In Journal of Nature Methods, vol. 11, Issue 5, May 2014, pp. 499-507.
Barthel, et al., "Enhancing Terminal Deoxynucleotidyl Transferase Activity on Substrates with 3' Terminal Structures for Enzymatic De Novo DNA Synthesis", In Journal of Genes, vol. 11, Issue 1, Jan. 16, 2020, pp. 1-9.
Bellare, et al., "Electrochemical Signal-triggered Release of Biomolecules Functionalized with His-tag Units", In Journal of Electroanalysis, vol. 31, Issue 11, Jul. 18, 2019, pp. 2274-2282.
Bollum, FJ., "Terminal Deoxynucleotidyl Transferase", In Journal of The Enzymes, vol. 10, Jan. 1, 1974, pp. 145-171.
Calvert, Paul, "Inkjet Printing for Materials and Devices", In Journal of Chemistry of materials, vol. 13, Issue 10, Oct. 15, 2001, pp. 3299-3305.
Chu, et al., "Assessing histidine tags for recruiting deoxyribozymes to catalyze peptide and protein modification reactions", In Journal of Organic & biomolecular chemistry, vol. 14, Issue 20, Apr. 27, 2016, pp. 4697-4703.
Costi, et al., "New Nucleotide-Competitive Non-Nucleoside Inhibitors of Terminal Deoxynucleotidyl Transferase: Discovery, Characterization, and Crystal Structure in Complex with the Target", In Journal of Medicinal Chemistry, Aug. 22, 2013, pp. 7431-7441.
Dimopoulou, et al., "Storing Digital Data Into DNA: A Comparative Study of Quaternary Code Construction", In Proceedings of IEEE International Conference on Acoustics, Speech and Signal Processing (ICASSP), May 4, 2020, pp. 4332-4336.
Gangarde, et al., "Amphiphilic Small Molecule Assemblies to Enhance the Solubility and Stability of Hydrophobic Drugs", In Journal of ChemRxiv, Feb. 10, 2020, pp. 1-7.
Kobayashi, et al., "Enzymatic synthesis of ligand-bearing DNAs for metal-mediated base pairing utilising a template independent DNA polymerase", In Journal of Chemical Communications, vol. 52, Issue 19, 2016, 18 Pages.
Liu, et al., "pH-Responsive carriers for oral drug delivery: challenges and opportunities of current platforms", In Journal of Drug Delivery, vol. 24, Issue 1, Feb. 14, 2017, pp. 569-581.
Nguyen, et al., "Long-Term Stability and Integrity of Plasmid-Based DNA Data Storage", In Journal of Polymers, vol. 10, Issue 1, Jan. 1, 2018, 10 Pages.
Organick, et al., "Random Access in Large-Scale DNA Data Storage", In The Journal of Nature Biotechnology, vol. 36, Issue No. 3, Mar. 2018, pp. 242-248.
Pandey, et al., "Inhibition of terminal deoxynucleotidyl transferase by adenine dinucleotides", In Journal of FEBS letters, vol. 213, No. 1, Mar. 9, 1987, pp. 204-208.

(56) References Cited

OTHER PUBLICATIONS

"International Search Report and Written Opinion Issued in PCT Application No. PCT/US20/038020", dated Sep. 21, 2020, 12 Pages.
"International Search Report and Written Opinion Issued in PCT Application No. PCT/US21/044861", dated Jan. 24, 2022, 17 Pages.
"International Search Report and Written Opinion Issued in PCT Application No. PCT/US21/028273", dated Aug. 27, 2021, 11 Pages.
US 11,305,253, 7/2007, Tathagato Rai Dastidar (withdrawn)
"Non Final Office Action Issued in U.S. Appl. No. 16/435,363", dated Mar. 8, 2023, 10 Pages.
"Non Final Office Action Issued in U.S. Appl. No. 17/815,380", dated Mar. 9, 2023, 8 Pages.
Kim, et al., "Hierarchical gene synthesis using DNA microchip oligonucleotides", In Journal of Biotechnology, vol. 151, Issue 4, Feb. 20, 2011, pp. 319-324.
"Non Final Office Action Issued in U.S. Appl. No. 16/886,638", dated Aug. 30, 2022, 9 Pages.
"Non Final Office Action Issued in U.S. Appl. No. 16/435,363", dated Apr. 18, 2022, 9 Pages.
"Notice of Allowance Issued in U.S. Appl. No. 16/886,638", dated Jan. 26, 2023, 8 Pages.
"Non Final Office Action Issued in U.S. Appl. No. 17/086,055", dated Jan. 19, 2023, 12 Pages.
Moore, et al., "Selective Release of DNA from the Surface of Indium-Tin Oxide Thin Electrode Films using Thiol-Disulfide Exchange Chemistry", In Journal of Analytical Chemistry, vol. 79, Issue 5, Mar. 1, 2007, pp. 2050-2057.
"Final Office Action Issued in U.S. Appl. No. 16/435,363", dated Nov. 10, 2022, 17 Pages.
"Final Office Action Issued in U.S. Appl. No. 17/086,055", dated Jul. 13, 2023, 13 Pages.

\* cited by examiner

ENCODING WITHOUT HOMOPOLYMERS

ENCODING WITH HOMOPOLYMERS

ســــــــــــــــــــــــــــــــــــــــــ

ARRAY-BASED ENZYMATIC OLIGONUCLEOTIDE SYNTHESIS

BACKGROUND

Synthetic oligonucleotides, also referred to as polynucleotides, such as deoxyribonucleic acid (DNA) and ribonucleic acid (RNA) have uses in medicine, molecular biology, nanotechnology, data storage, as well as other applications. Enzymatic oligonucleotide synthesis has emerged as an alternative to the long-standing nucleoside phosphoramidite method for the synthesis of polynucleotides. Enzymatic synthesis is performed with a template independent polymerase such as terminal deoxynucleotide transferase (TdT) rather than a series of chemical reactions. Enzymatic polynucleotide synthesis has advantages over the nucleoside phosphoramidite method because it is performed in an aqueous environment and does not use toxic organic chemicals. Enzymatic synthesis also has the potential to create longer polynucleotides than the nucleoside phosphoramidite method.

However, enzymes such as TdT add nucleotides in an unregulated manner that creates variable length homopolymers as a result of adding the same nucleotide multiple times during a single synthesis cycle. With the established nucleoside phosphoramidite method, each synthesis cycle reliably adds only a single nucleotide. Thus, due to the potential for homopolymer addition, it is difficult to create polynucleotides with specific single-base sequences using enzymatic synthesis.

Some applications for synthetic polynucleotides such as data storage do not necessarily require single-base precision or accuracy. However, even though single-based position is not required, implementing data storage with polynucleotides at scale will use a large number of polynucleotides with different sequences to encode vast amounts of data. Therefore, techniques and systems for efficient and high throughput enzymatic synthesis of polynucleotides are desirable. Techniques for encoding digital information in polynucleotides that include homopolymers of variable, and potentially unknown length, are also desirable. This disclosure is made with respect to these and other considerations.

SUMMARY

This disclosure provides methods and systems for array-based enzymatic synthesis of polynucleotides. Spatially addressable control of reaction conditions on the surface of an array allows for synthesis of multiple polynucleotides with different sequences. The spatial control may be provided by removing protecting groups from nucleotides only at specific spots on the array. The spatial control may alternatively be provided by controlling polymerization activity so that the template independent polymerase actively adds nucleotides only at specific spots on the array. Changing the locations where polymerization is able to occur during each cycle of synthesis allows the polynucleotides at different spots on the surface of the array to be synthesized with different nucleotide sequences.

Array-based synthesis of polynucleotides using template independent polymerases overcomes limitations of previous enzymatic synthesis techniques that use beads in a test tube as a solid substrate. All polynucleotides synthesized in the same test tube, or another undifferentiated reaction chamber, will have the same sequence of nucleotides. Systems that require a different, physically-isolated reaction environment such as different test tubes to create polynucleotides with different nucleotide sequences are difficult to scale and have limited throughput. Array-based synthesis provides addressability and site-specific adaptation of reaction environments by using a rigid or semi-rigid surface that is substantially flat as the solid substrate for polynucleotide synthesis. This design provides multiple separately adjustable reaction environments with a structure that is more compact and requires less physical manipulation than a comparable system using beads and test tubes.

This disclosure also provides methods and systems for encoding digital information in polynucleotides synthesized using a template independent polymerase. Template independent polymerases such as TdT do not create polynucleotides with specific base-by-base level of sequence control but rather add homopolymers of variable length. Although the order of which nucleotides are incorporated can be controlled, it is difficult to precisely control the number of nucleotides added during a single cycle of synthesis. Thus, many existing techniques for encoding digital information in a sequence of nucleotide bases may be unable to decode polynucleotides that include homopolymers of variable and unknown length.

The encoding techniques described herein collapse homopolymers in sequence strings down to a single nucleotide or to a shorter homopolymer. If the original encoding scheme converts digital information to a sequence of nucleotide bases without homopolymers, then the decoding will reduce any string of the same nucleotide to a single instance of that nucleotide. For example, the nucleotide string ATTTA would be converted to the nucleotide string ATA before further processing.

If the length of the homopolymers can be controlled at least approximately, then the length of the homopolymer generated by the template independent polymerase may be converted to a shorter homopolymer with a length that depends on the length of the homopolymer in the original nucleotide string. For example, if the enzyme is regulated so that each cycle of synthesis adds approximately four nucleotides (i.e., an average extension length of four nucleotides) a homopolymer of length eight would be interpreted as two occurrences of the specified nucleotide. An example of this is collapsing the nucleotide string GGGGGGGG to the shorter homopolymer GG.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
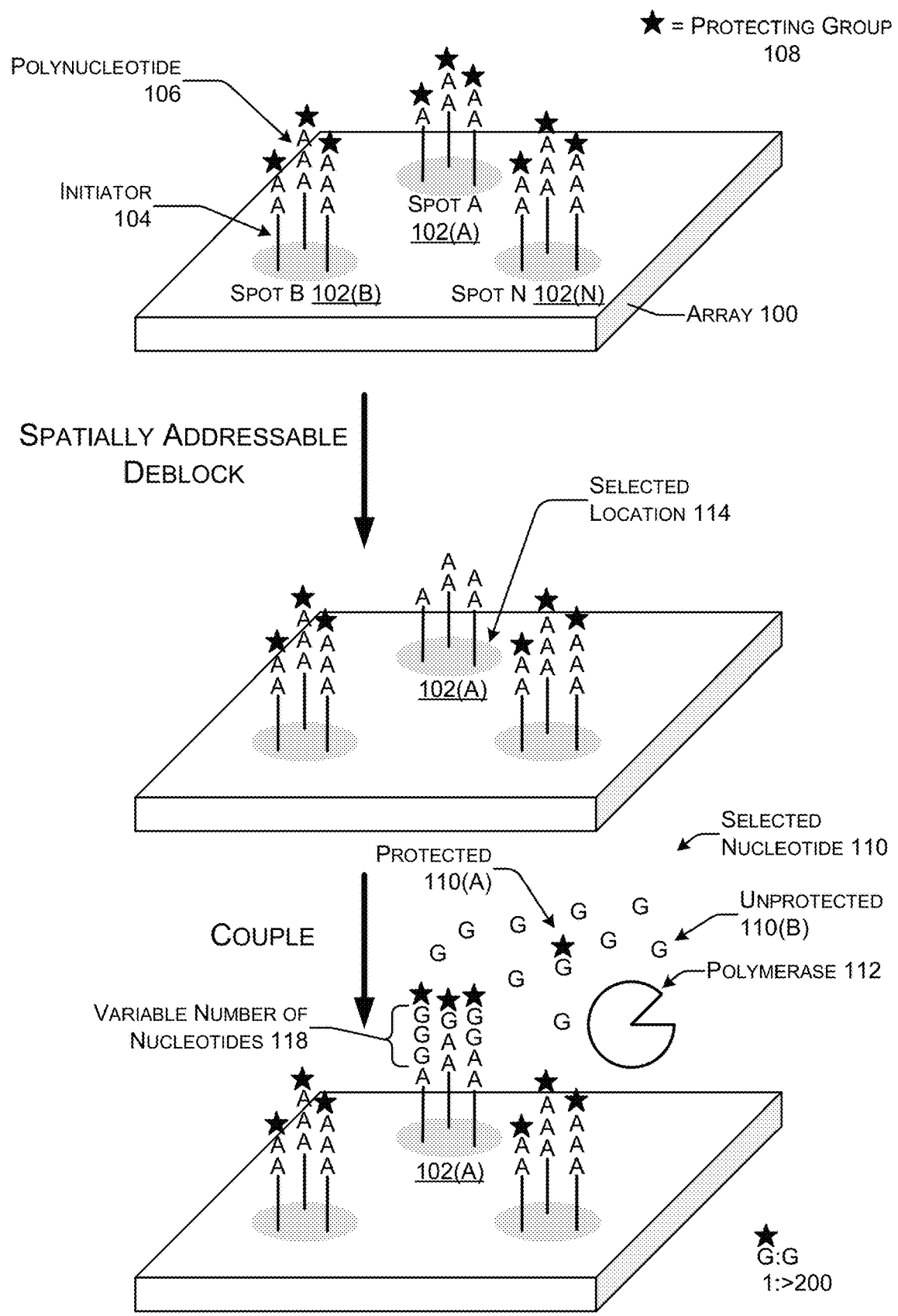
FIG. 1 shows an array during three different stages of enzymatic polynucleotide synthesis using a mixture of unprotected nucleotides and nucleotides attached to a protecting group.

This disclosure provides a method and device to overcome scaling issues with current techniques for enzymatic polynucleotide synthesis by synthesizing polynucleotides on a spatially addressable array. This disclosure also provides a method and device for encoding digital information in polynucleotides that are synthesized using an unregulated enzymatic process which may add more than one nucleotide during a single cycle of synthesis.

Polynucleotides, also referred to as oligonucleotides, include both DNA, RNA, and hybrids containing mixtures of DNA and RNA. DNA includes nucleotides with one of the four natural bases cytosine (C), guanine (G), adenine (A), or thymine (T) as well as unnatural bases, noncanonical bases, and/or modified bases. RNA includes nucleotides with one of the four natural bases cytosine, guanine, adenine, or uracil (U) as well as unnatural bases, noncanonical bases, and/or modified bases. Nucleotides include both deoxyribonucleotides and ribonucleotides covalently linked to one or more phosphate groups.

Template independent polymerases are DNA or RNA polymerases that perform de novo oligonucleotide synthesis without use of a template strand. Currently known template independent polymerases include TdT and tRNA nucleotidyltransferase. TdT includes both the full-length wild-type enzyme, as well as modified enzymes that are truncated or internally modified. One example of modified TdT is provided in U.S. Pat. No. 10,059,929. An example of truncated TdT is provided in U.S. Pat. No. 7,494,797. Thus, template independent polymerase as used herein includes full-length wild-type, truncated, or otherwise modified TdT, tRNA nucleotidyltransferase, and any subsequently discovered or engineered polymerases that can perform template independent synthesis of polynucleotides. Template independent polymerase as used herein does not encompass modifications of TdT or tRNA nucleotidyltransferase that render those enzymes incapable of performing template independent nucleotide polymerization.

TdT is a protein that evolved to rapidly catalyze the linkage of naturally occurring deoxynucleotide triphosphates (dNTPs). TdT adds nucleotides indiscriminately to the 3' hydroxyl group at the 3' end of single-stranded DNA. TdT performs unregulated synthesis adding any available dNTP. TdT uses an existing single-stranded polynucleotide referred to as an "initiator" as the starting point for synthesis. Initiators as short as three nucleotides have been successfully used with TdT for enzymatic synthesis of DNA. Suitable initiator length ranges from three nucleotides to about 30 nucleotides or longer. During polymerization, the template independent polymerase holds a single-stranded DNA strand (which initially is only the initiator but grows as synthesis proceeds) and adds dNTPs in a 5'-3' direction. TdT activity is maximized at approximately 37° C. and performs enzymatic reactions in an aqueous environment.

Because TdT performs unregulated synthesis, using this enzyme to create a polynucleotide with a pre-specified arbitrary sequence requires regulation and control of the TdT activity. One technique to regulate TdT activity is limiting the available nucleotides to only a single type of deoxynucleoside triphosphate (dNTP) or nucleoside triphosphate (NTP) (e.g., only deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP)). Thus, providing only one choice forces the polymerase to add that type of nucleotide.

However, this does not prevent TdT from adding that nucleotide multiple times thereby creating homopolymers. Techniques for limiting homopolymer creation by TdT include using nucleotides with removable protecting groups that prevent addition of more than one nucleotide at a time. See U.S. Pat. No. 10,059,929. Another technique to force single-nucleotide addition is covalently coupling a single nucleotide to each TdT enzyme so that the TdT acts as its own protecting group preventing further chain elongation. See Sebastian Palluck et al., De novo *DNA synthesis using polymerase-nucleotide conjugates,* 36(7) Nature Biotechnology 645 (2018) and WO 2017/223517 A1. A third technique restricts homopolymer formation by limiting the available quantity of nucleotides through competition for dNTPs between TdT and an enzyme that degrades dNTPs. See Henry H. Lee et al., *Terminator free template-independent Enzymatic DNA Synthesis for Digital Information Storage,* 10(2383) Nat. Comm. (2019) and WO 2017/176541 A1.

Although techniques exist for limiting the "extension length" or average number of nucleotides added during a cycle of synthesis, current methods for enzymatic nucleotide synthesis involve initiators attached to beads in a test tube or other discrete reaction chamber. The reaction chamber is flooded with an aqueous solution containing TdT and only one type of dNTP. Once coupling has taken place, the TdT and any free dNTPs are washed away. The beads are incubated in a second step with TdT and a different dNTP. The process continues creating DNA molecules with sequence specified by the order in which the different dNTPs are added. Depending on the control technique used, TdT may add a single nucleotide or an uncontrolled number of the same nucleotide during each cycle synthesis. This process does not scale well for applications that require high throughput synthesis of multiple polynucleotides with different sequences.

One relatively recent application for synthetic polynucleotides that benefits from high throughput synthesis is data storage. Polynucleotides such as DNA may be used to store digital information by designing a sequence of nucleotide bases—adenine (A), cytosine (C), guanine (G), and thymine (T)—that encodes the zeros and ones of digital information. Advantages of using DNA rather than another storage media for storing binary data include information density and longevity. The sequence of nucleotide bases is designed on a computer and then DNA molecules with that sequence are generated by an oligonucleotide synthesizer. The DNA may be stored and later read by polynucleotide sequencer to retrieve the binary data.

There are various techniques and encoding schemes known to those of skill in the art for using nucleotide bases to represent binary data. See Lee Organick et al., *Random Access in Large-Scale DNA Data Storage*, 36:3 Nat. Biotech. 243 (2018), and Henry H. Lee et al., *Terminator-free template-independent Enzymatic DNA Synthesis for Digital Information Storage*, 10(2383) Nat. Comm. (2019), WO 2018/148260 A1 and U.S. Pat. App. Pub. No. 2017/0141793. However, these encoding techniques either require enzymatic synthesis techniques that constrain the extension length to a single nucleotide or accommodate homopolymers in the encoding by sacrificing information density such as by encoding data in trits rather than using an alphabet with four (or more) letters.

FIG. 1 shows an illustrative representation of an array 100 for enzymatic polynucleotide synthesis at three different stages of the synthesis cycle. The array 100 provides a solid support for solid-phase synthesis of polynucleotides. Solid-phase synthesis is a method in which molecules are anchored to a solid support material and synthesized while attached to the solid support.

The array 100 may be formed from a silicon chip, glass (e.g., controlled porous glass (CPG)), an insoluble polymer, or other material. The array 100 being a generally flat two-dimensional surface provides for addressable, site-specific manipulations at specified locations (e.g., represented in terms of x- and y-coordinates) on the surface of the array 100. The array 100 may be an electrochemically inert surface or it may include an array of spatially addressable microelectrodes. One example of a suitable array with microelectrodes is provided in U.S. patent application Ser. No. 16/435,363 filed on Jun. 7, 2019, with the title "Reversing Bias in Polymer Synthesis Electrode Array."

The array 100 may be covered with a plurality of spots 102(A), 102(B), . . . , 102(N) at which initiators 104 are attached. Although only three spots 102(A), 102(B), 102(N) are shown in this illustrative representation many thousands or hundreds of thousands of spots may be present on a typical array 100. The size of a single spot 102 can be smaller than about 1 cm$^2$, smaller than 1 mm$^2$, smaller than 0.5 mm$^2$, and in some implementations about 0.125 to 0.5 mm$^2$.

The initiators 104 may be attached to the array 100 using any known technique for anchoring single-stranded DNA or RNA to a solid support such as techniques used in conventional solid-phase synthesis of oligonucleotides or used for creation of DNA microarrays. For example, the initiators 104 may be spotted onto the array 100 by use of a robot to "print" pre-designed nucleotide sequences using fine-pointed pins, needles, or ink-jet printing onto a chemical matrix surface using surface engineering. Other methods employ photo-activated chemistry and masking to synthesize the initiators 104 one nucleotide at a time on the solid surface of the array 100 with a series of repeated steps to build up the initiators 104 at designated locations.

The initiator 104 is a single-stranded polynucleotide chain. The length of the initiator 104 may be about 3-30 nucleotides, about 15-25 nucleotides, or about 20 nucleotides. The initiator 104 is not shown to scale. Enzymatic synthesis begins at a 3' terminal nucleotide on the end of the initiator 104 and proceeds by adding one or more nucleotides to the initiator 104. The most recently added nucleotide becomes the 3' terminal nucleotide and the synthesis cycle can proceed again.

All of the initiators 104 attached to the array 100 may have the same or approximately the same nucleotide sequence or one or more of the initiators 104 may have different sequences from the others. The sequence of any one or more of the initiators 104 may be a random sequence of nucleotides. The initiators 104 may also be constructed with non-random sequences such as, for example, sequences that are cleaved by a restriction endonuclease. Cleavage of the initiators 104 is one way to release completed polynucleotides 106 from the surface of the array 100. The sequences of the initiators 104 may also be designed or used as primer binding sites for subsequent amplification (e.g., polymerase-chain reaction (PCR) amplification) of fully synthesized polynucleotides.

Each spot 102 on the array 100 may contain many tens or hundreds of initiators 104 although for simplicity only three initiators 104 are shown on each spot 102 in this illustrative representation. Each initiator 104 attached to the same spot 102 is subject to the same spatially addressable control. Stated differently, any spatially addressable manipulations applied to the array 100 performed at the resolution of individual spots 102. However, the polynucleotides 106 synthesized on the same spot 102 do not necessarily have the same single nucleotide sequence because of the formation of variable length homopolymers. In this illustrative representation, a first cycle of synthesis has added from one to three adenine nucleotides (A) to the 3' end of the initiators 104.

At the start of synthesis, each of the 3' nucleotides on the ends of the initiators 104 may be capped with a protecting group 108 represented in FIG. 1 as small stars. Each cycle of synthesis may end when all or substantially all of the polynucleotides 106 attached to the array 100 are capped with a protecting group 108. The protecting group 108 prevents further addition of nucleotides, and thus, is one way to regulate synthesis of the polynucleotides 106.

The protecting groups 108 may attach to the 3' hydroxyl group or to another location on a dNTP, NTP, or a nucleotide attached to the initiator 104. The protecting groups 108 may be any kind of moiety or group that prevents a polymerase from adding additional nucleotides. As is known to those skilled in the art, there are various techniques for removing protecting groups 108 based on the specific composition of the protecting group 108 and the reaction environment. For example, a protecting group 108 may be removed by addition of chemicals (e.g., an acid or base solution), may be photolabile and cleaved by exposure to light, may be thermolabile and cleaved by exposure to heat, or may be cleaved by an enzyme.

Some examples of protecting groups 108 include esters, ethers, carbonitriles, phosphates, carbonates, carbamates, hydroxylamine, borates, nitrates, sugars, phosphoramide, phosphoramidates, phenylsulfenates, sulfates, sulfones, and amino acids. See Michael L. Metzker et al., *Termination of DNA Synthesis by Novel 3'-modified-deoxyribonucleoside 5'-triphosphates*, 22(20) Nucl. Acids Res., 4259 (1994) and U.S. Pat. Nos. 5,763,594, 6,232,465, 7,414,116, and 7,279,563. Other types of protecting groups 108 include 3'-O-amino, 3'-O-allyl, and a 3'-O-azidomethyl groups. Examples of protecting groups 108 also include O-phenoxyacetyl; O-methoxyacetyl; O-acetyl; O-(p-toluene)-sulfonate; O-phosphate; O-nitrate; O-[4-methoxy]-tetrahydrothiopyranyl; O-tetrahydrothiopyranyl; O-[5-methyl]-tetra-hydrofuranyl; O[2-methyl,4-methoxy]-tetrahydropyranyl; O-[5-methyl]-tetrahydropyranyl; and O-tetrahydrothiofuranyl. See U.S. Pat. No. 8,133,669 for a discussion of these protecting groups. Additional examples of protecting groups are provided in U.S. patent application Ser. No. 16/230,787 filed on Dec. 21, 2018, with the title "Selectively Controllable Cleavable Linkers."

Selectively addressable deblocking of the protecting groups 108 that are capping the polynucleotides 106 on one or more of the spots 102, in this example spot 102(A), regulates where on the surface of the array 100 nucleotides may be added during the next synthesis cycle. In a synthesis cycle, the surface of the array 100 may be flooded with a selected nucleotide 110 (i.e., a nucleotide having a specified base such as A, C, G, T, or U) and a polymerase 112. Controlling which spots 102 on the array 100 have the protecting groups 108 removed thereby defines a selected location 114 for addition of the next type of nucleotide.

The selected location 114 may be any one or more locations that are contiguous or separate on the surface of the array 100. The selected location 114 may be a single spot 102, a group of spots 102 located adjacent to each other, or multiple disparate spots 102 spread across the surface of the array 100. In some implementations, the selected location 114 has an area less than about 10,000 μm² or less than 100 μm². The resolution or minimum size of the selected location 114 may be a single spot 102.

The polymerase 112 is a template independent polymerase such as TdT or tRNA nucleotidyltransferase. The template independent polymerase 112 may be obtained from a number of sources such as isolation from calf thymus or from a recombinant source (e.g., a genetically modified *E. coli* strain). The template independent polymerase 112, selected nucleotide 110, and other entities that are not attached to the array 100 are present in an aqueous solution (not shown) that covers the surface of the array 100. The aqueous solution may include buffers, salts, electrolytes, and the like. For example, the aqueous solution may include TdT buffer and a $CoCl_2$ solution, The selected nucleotide 110 in this illustrative representation includes the base guanine (G) such as dGTP or GTP. The selected nucleotide 110 may be provided in a nucleotide mixture that that includes both protected nucleotides 110(A) that are attached to a protecting group 108 and unprotected nucleotides 110(B) that are not attached to a protecting group 108. The selected nucleotide 110 including both the protected nucleotides 110(A) and that unprotected nucleotides 110(B) may be provided in excess so that the availability of the selected nucleotide 110 is not a limiting factor. So long as the selected nucleotide 110 is available and reaction conditions permit the polymerase 112 to function, the template independent polymerase 112 will continually incorporate unprotected nucleotides 110(B) until a protected nucleotide 110(A) is incorporated.

Thus, the nucleotide ratio 116 of protected nucleotides 110(A) to unprotected nucleotides 110(B) may be tuned to adjust the extension length. In this illustrative representation the extension length, the number of "G" added, is one, two, or three. In actual synthesis, the extension length could be much longer and include a greater range. Thus, the extension length for the polynucleotides 106 at spot A 102(A) is a variable number of nucleotides 118 with an average value of two.

This variation exists because the selection of a protected nucleotide 110(A) or an unprotected nucleotide 110(B) to incorporate at the end of a growing polynucleotide 106 is essentially random based on diffusion of the nucleotides throughout the aqueous solution covering the array 100. Thus, under a given set of reaction conditions the extension length for a population of polynucleotides 106 will be a variable number of nucleotides 118 with a distribution concentrated around a mean extension length. The reaction conditions include temperature, time, and the concentrations of the protected nucleotide 110(A), of the unprotected nucleotide 110(B), and of the template independent polymerase 112.

Thus, unless context indicates otherwise, "extension length" refers to the average extension length for a given set of reaction conditions. This variation in extension length for individual ones of the polynucleotides 106 is the reason why a population of polynucleotides 106 synthesized under the same reaction conditions include homopolymers with a variable number of nucleotides 118. This is different from a homopolymer with a fixed number of nucleotides that is the same throughout a population of polynucleotides.

Adjusting the nucleotide ratio 116 of the protected nucleotides 110(A) to unprotected nucleotides 110(B) is a way to tune or adjust the extension length. As the relative concentration of protected nucleotides 110(A) increases, the extension length decreases. Conversely, as the relative concentration of unprotected nucleotides 110(B) increases, the extension length increases. One example nucleotide ratio 116 is one protected nucleotide 110(A) for every 200 or more unprotected nucleotides 110(B).

Using a mixture that includes unprotected nucleotides 110(B) rather than only protected nucleotides 110(A) provides cost benefits because unprotected nucleotides 110(B) are less expensive. For example, dNTPs with protecting groups such as CleanAmp® dNTPs available from TriLink® Biotechnologies cost approximately 2.5 times more than equivalent unprotected dNTPs.

Spatially addressable deblocking of the protecting groups 108 is one of many possible techniques for controlling where on the array 100 polynucleotide synthesis is able to occur. In implementations where protecting groups 108 are not used, the selected location 114 may be defined by areas on the array 100 where conditions are changed such that the template independent polymerase 112 is active. Localized template independent polymerase 112 activation may be achieved by regulating the oxidation state of a metal cofactor that catalyzes activity of the polymerase 112. U.S. patent application Ser. No. 16/543,433 filed on Aug. 16, 2019, with the title "Regulation of Polymerase Using Cofactor Oxidation States" describes the use of cofactor oxidation states to control template independent polymerase activity.

Other techniques for controlling the activity of the template independent polymerase 112 include use of an inkjet printer or microelectrode array to selectively make available a reagent or induce a change that is necessary for template independent polymerase 112 activity. For example, spatially addressable addition of the selected nucleotide 110 or a metal cofactor can be used to define a selected location 114. Cleavage of a protecting group attached to the template independent polymerase 112 only at the selected location 114 may be used to regulate the locations of template independent polymerase 112 activity.

Figure 2:
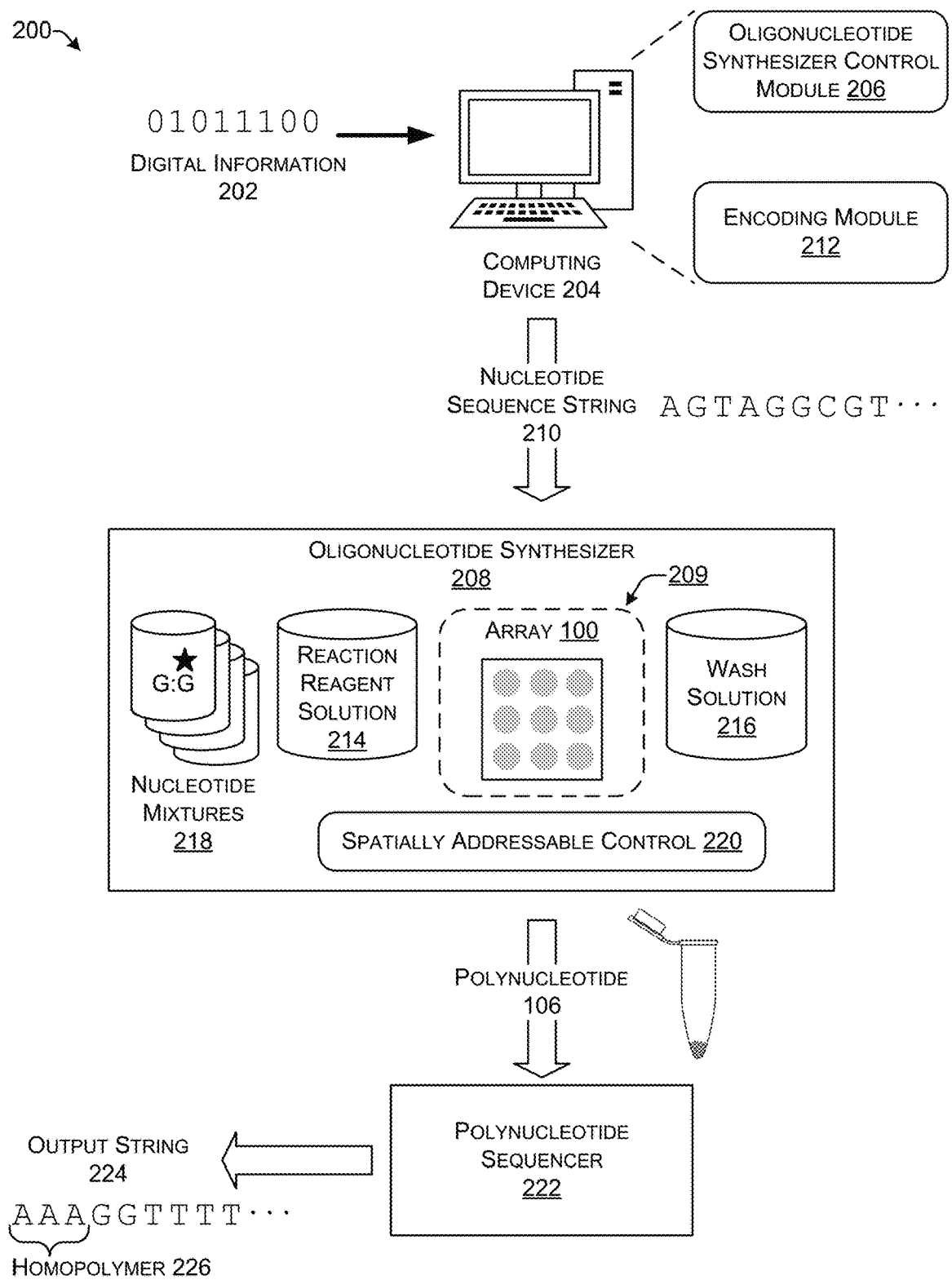
FIG. 2 is an architecture of a system for encoding digital information in a polynucleotide synthesized on an array by a template independent polymerase and for sequencing the polynucleotide to generate an output string that can be decoded to recover the digital information.

FIG. 2 shows an illustrative architecture of a system 200 for implementing aspects of this disclosure. In the system 200 digital information 202 representing, for example, the data from a computer file is provided to a computing device 204. The computing device 204 may be implemented as any type of conventional computing device such as a desktop computer, a laptop computer, a server, a hand-held device, or the like. The computing device 204 may be a standalone device or may be integrated with another device present in the system 200.

The computing device 204 includes an oligonucleotide synthesizer control module 206. The oligonucleotide synthesizer control module 206 provides instructions that can control operation of an oligonucleotide synthesizer 208. The instructions may communicate to the oligonucleotide synthesizer 208 a nucleotide sequence string 210 for synthesis. The nucleotide sequence string 210 is an electronic representation of specific nucleotides bases. In this illustrative system 200, the nucleotide sequence string 210 begins with the deoxyribonucleotides AGTAGGCGT.

The nucleotide sequence string 210 is generated by an encoding module 212 in the computing device 204. The encoding module 212 converts the digital information 202 into a nucleotide sequence string 210 according to an encoding scheme. The encoding scheme may include error correction, redundancy, and addition of metadata such as nucleotide sequences that function as tags for random access. Encoding schemes for representing digital information 202 as a nucleotide sequence string 210 are known to those of skill in the art. In an implementation, the encoding module 212 generates a nucleotide sequence string 210 that does not include homopolymers. Thus, every position in the string is followed by a different value. However, in a different implementation, the encoding module 212 generates a nucleotide sequence string 210 that includes homopolymers.

The oligonucleotide synthesizer 208 is a device that performs automated solid-phase synthesis of polynucleotides on an array 100. The array 100 may be located within a reaction chamber 209 or container capable of maintaining an aqueous environment in contact with the surface of the array 100. The oligonucleotide synthesizer 208 may also include a heater to control the temperature of the aqueous solution in the reaction chamber 209.

During each synthesis cycle, the oligonucleotide synthesizer 208 may deliver a reaction reagent solution 214 followed by a wash solution 216 to the reaction chamber 209 containing the array 100. The reaction reagent solution 214 and the wash solution 216 may be delivered to the array 100 through fluid delivery pathways. The fluid delivery pathways may be implemented by tubes and pumps, microfluidics, laboratory robotics, or other equipment and techniques.

The reaction reagent solution 214 is an aqueous solution that contains the template independent polymerase 112, the selected nucleotide 110, and a buffer or salt. The selected nucleotide 110 may be added to the reaction reagent solution 214 from one of several nucleotide mixtures 218. Each of the nucleotide mixtures 218 includes only one type of nucleotide (e.g., dATP, dGTP, dCTP, or dTTP) as a mixture of protected nucleotides 110(A) and unprotected nucleotides 110(B). Each of the nucleotide mixtures 218 may include a specific nucleotide ratio 116. The specific nucleotide ratio 116 may be different for different types of nucleotides due to variations in polymerization kinetics depending on the base attached to the nucleotide sugar. The base-specific nucleotide ratios 116 may be selected so that the extension length is the same for each type of nucleotide. Protected nucleotides 110(A) that are not mixed with unprotected nucleotides 110(B) may also be available to the oligonucleotide synthesizer 208. The reaction reagent solution 214 may be created with only protected nucleotides 110(A) to synthesize sequences with precise base-by-base level control of the synthesized sequence.

The buffer may be any one of a number of aqueous buffers that are compatible with the template independent polymerase 112 such as, for example, phosphate-buffered saline (PBS). PBS is a water-based salt solution containing disodium hydrogen phosphate, sodium chloride and, in some formulations, may also include one or more of potassium chloride and potassium dihydrogen phosphate. The buffer may be an aqueous solution including 1 M potassium cacodylate, 125 mM Tris-HCl, 5 mM CoCl, and 1.25 mg/ml BSA, at pH 6.6. Other examples of aqueous buffers known to those of ordinary skill in the art include HEPES, MOPS, PBS, PBST, TAE, TBE, TBST, TE, and TEN. See Vincent S. Stoll & John S. Blanchard, *Buffers: Principles and Practice,* 182 Meth. Enzoml., 24 (1990).

The wash solution 216 may be added to the array 100 as a step of the polynucleotide synthesis process. The wash solution 216 is water (e.g., DI (deionized) water) or an aqueous solution that contains at least one of a salt or a buffer. The salt or the buffer may be the same as the salt or buffer used in the reaction reagent solution 214. The wash solution 216 removes the reaction reagent solution 214 from the surface of the array 100 which remove any remaining free nucleotides and prevents contamination between separate cycles of synthesis.

In implementations that do not use protecting groups 108, a technique other than capping polynucleotide strands with a protecting group 108 is used to stop the activity of the template independent polymerase 112. Other techniques for stopping the template independent polymerase 112 from continually adding nucleotides include removing a necessary component of the polymerization reaction from the reaction chamber 209 and inactivating a necessary component of the polymerization reaction.

Displacing the reaction reagent solution 214 with the wash solution 216 removes both the template independent polymerase 112 the selected nucleotide 110. Thus, adding the wash solution 216 is one way to stop the activity of the template independent polymerase 112. Other ways to stop the activity of the template independent polymerase 112 include raising the temperature of the aqueous solution in the reaction chamber 209 to a temperature that inactivates the template independent polymerase 112. For example, the template independent polymerase 112 may be inactivated at temperatures above about 70° C., above about 65° C., or above about 60° C. Addition of a chelator such as EDTA that coordinates with metal cofactors necessary to catalyze enzymatic activity is another technique that may be used to stop the activity of the template independent polymerase 112. Denaturing the template independent polymerase 112 with a surfactant such as sodium dodecyl sulfate (SDS) is yet another way to inactivate the template independent polymerase 112.

Enzymatic polynucleotide synthesis without the use of protecting groups 108 achieves spatially addressable synthesis through use of a spatially addressable control 220. The spatially addressable control 220 is used to designate the selected location 114 during each cycle of synthesis. The spatially addressable control 220 may be implemented as an array of spatially addressable microelectrodes embedded in or beneath the array 100. The microelectrodes may be implemented with any known technology for creating microelectrodes such as complementary metal-oxide-semiconductor (CMOS) technology. CMOS may include metal-oxide-semiconductor field-effect transistors (MOSFETs) made through a triple-well process or by a silicon-on-insulator (SOI) process. A series of controllable gates/transistors implemented with CMOS circuits can be controlled to inject charge at any location on the surface of the array 100.

Each spatially addressable microelectrode in the array 100 may be independently addressed allowing the creation of arbitrary and variable voltage microenvironments across the surface of the array 100. Changes in the voltage microenvironments can promote or inhibit polynucleotide synthesis depending identity of species in the reaction reagent solution 214 such as metal cofactors. Thus, a microelectrode array can control where on the surface of the array 100 polynucleotide synthesis occurs.

The spatially addressable control 220 may be an inkjet printer that is able to precisely apply small volumes of reagents to specific locations on the surface of the array 100. Techniques for using inkjet printing to precisely deliver chemical reagents to selected locations on a surface of an array are well-known to those of ordinary skill in the art. The chemical reagent delivered by the inkjet printer may be used to promote or inhibit polynucleotide synthesis. Thus, an inkjet printer can control where on the surface of the array 100 polynucleotide synthesis occurs.

The spatially addressable control 220 may be a light array that is capable of directing light to specific locations on the surface of the array 100. Light from the light array may excite a photocatalyst that performs a photoredox reaction or that cleaves a photolabile linker. The light array may include a photomask or digital micromirror device to direct the light. Thus, a light array can control where on the surface of the array 100 polynucleotide synthesis occurs.

The spatially addressable control 220 may use a technique to physically block the template independent polymerase 112 or the selected nucleotide 110 from accessing areas of the array that are not the selected location 114. Doing so limits polymerization to the selected location 114 on the array 100. In one implementation, the template independent polymerase 112 and/or the selected nucleotide 110 are blocked from some regions of the array 100 by targeted and precise addition of the wash solution 216 (or another solution that does not contain the template independent polymerase 112 and/or nucleotides). The wash solution 216 may displace or dilute the template independent polymerase 112 and the selected nucleotide 110 where added thereby preventing polynucleotide synthesis. Microfluidics embedded in the array 100 may include pores or outlets collocated with the spots 102. Use of the microfluidics to deliver the wash solution 216 to one or more spots 102 during the incubation prevents polymerization on the initiators at those spots 102.

In one implementation, blocking access to regions of the array may be achieved by depositing or creating gas bubbles at the locations of one or more of the spots 102. The gas bubbles occupy the surface of the array 100 and remain in position due to surface tension of the reaction reagent solution 214. The array 100 may have a well or depression at the location a spot 102 which can stabilize the position of the gas bubble. Presence of a gas bubble displaces the reaction reagent solution 214 thereby preventing the template independent polymerase 112 and the selected nucleotide 110 from accessing initiators 104 covered by or contained within a gas bubble.

A gas bubble may be deposited on the surface of the array 100 at a specified location, such as at a given spot 102, by directing air, nitrogen, oxygen, carbon dioxide, or another gas through a small diameter tube. The location of the tube relative to the surface of the array 100 may be controlled by laboratory robotics or similar system capable of precision movements relative to two axes (e.g., x- and y-axis of the array 100). Hydrogen gas bubble may be created on the surface of a microelectrode array by activating one or more microelectrodes to hydrolyze water in the reaction reagent solution 214.

The spatially addressable control 220, no matter how implemented, may be operated by control circuitry in the oligonucleotide synthesizer 208. The control circuitry may be implemented as any type of circuitry suitable for controlling hardware devices such as a printed circuit board, microcontroller, a programmable logic controller (PLC), or the like. The control circuitry may receive instructions from the oligonucleotide synthesizer control module 206. The instructions may indicate the regions of the array 100 at which polynucleotide synthesis will occur. The control circuitry then causes the spatially addressable control 220 to remove protecting groups 108 or enable the activity of the template independent polymerase 112 at the selected location 114.

Ultimately the oligonucleotide synthesizer 208 creates a polynucleotide 106. A different polynucleotide sequence may be synthesized on each of the spots 102 on the array 100. The sequence of the polynucleotide 106 is specified by the nucleotide sequence string 210 received from the encoding module 212. However, due to the unregulated polymerization by the template independent polymerase 112, the polynucleotide 106 includes homopolymers that are not present in the nucleotide sequence string 210.

The polynucleotide 106 may be cleaved from the array 100 by severing a connection between the initiator 104 and the array 100 or by cleaving the initiator 104. The polynucleotide 106 free of the array 100 may then be stored in solution such as the wash solution 216, as a dried pellet in a tube, or any other technique for storage of polynucleotides 106. During storage, the polynucleotides 106 may serve to provided long-term "cold" storage for the digital information 202. The polynucleotide 106 may also be processed using any existing technique for processing polynucleotides including, but not limited to, PCR amplification of the polynucleotide 106 to increase the copy number. As is known to those of ordinary skill in the art, PCR amplification uses a forward and reverse primer to initiate polymerization of a template strand. Primer binding specificity is one factor in controlling the efficacy of PCR amplification. Thus, the sequence of the polynucleotide 106 that serves as a primer binding site may have less tolerance for incorporation of homopolymers than other regions of the polynucleotide 106. Accordingly, the regions of the polynucleotide 106 that may potentially function as primer binding sites can be created using a technique other than enzymatic synthesis or created with a reaction solution that contains only protected nucleotides 110(B) in order to achieve base-by base precision in the nucleotide sequence.

When it is time to recover the digital information 202, the polynucleotide 106 may be sequenced by a polynucleotide sequencer 222. Polynucleotide sequencers are well known to those of ordinary skill in the art. Many different techniques may be used to read the sequence of nucleotide bases in the polynucleotide 106. Common sequencing techniques include dideoxy sequencing reactions, next generation sequencing, and nanopore sequencing. Classic dideoxy sequencing reactions (Sanger method) use labeled terminators or primers and gel separation in slab or capillary electrophoresis.

Next generation sequencing refers to any of a number of post-classic Sanger type sequencing methods which are capable of high throughput, multiplex sequencing of large numbers of samples simultaneously. Current next generation sequencing platforms are capable of generating reads from multiple distinct nucleic acids in the same sequencing run.

Nanopore sequencing uses a small hole, a "nanopore," on the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

The polynucleotide sequencer 222 provides an output string 224 in an electronic format that can be manipulated by a computer such as, but not limited to, the computing device 204 to decode and recover the digital information 202. However, as described above, the output string 224 may include a homopolymer 226 (likely many homopolymers) that are not present in the nucleotide sequence string 210. The differences between the output string 224 and the nucleotide sequence string 210 make it difficult or impossible for many encoding schemes to recover the digital information 202 from polynucleotides 106 created by enzymatic synthesis.

Figure 3:
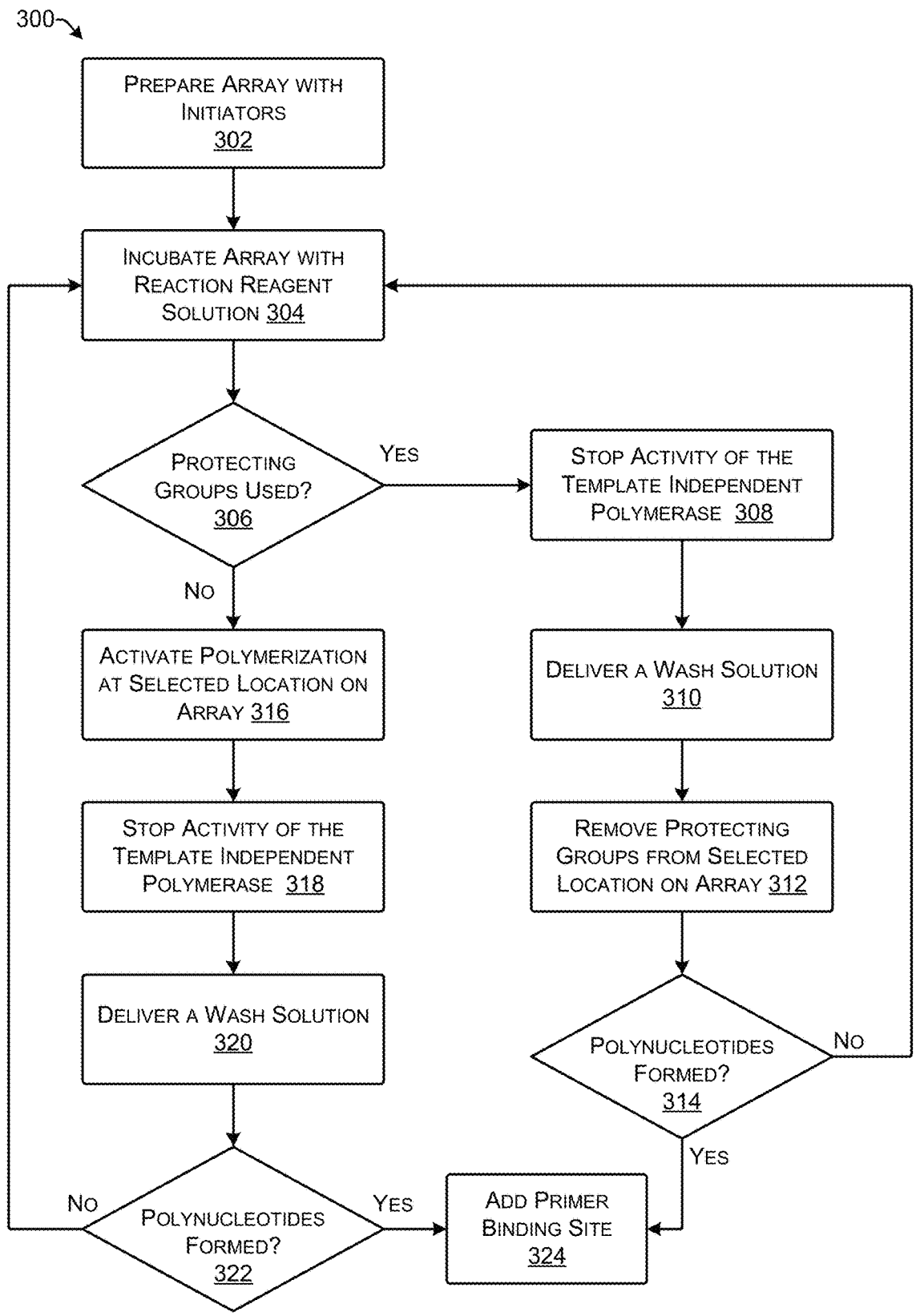
FIG. 3 is a flow diagram showing an illustrative process for array-based enzymatic synthesis of polynucleotides.

FIG. 3 shows process 300 for synthesizing polynucleotides on an array using a template independent polymerase. This process 300 may be implemented, for example, using any of the reactions, structures, and devices shown in FIGS. 1 and 2.

At 302, an array is prepared by the addition of one or more initiators. This results in the creation of an array that is covered with a plurality of initiators. The initiators are single-stranded nucleotides with a length of between about 3-30 nucleotides. A template independent polymerase uses the initiators as a starting point for polynucleotide synthesis by adding additional nucleotides to the 3' terminal nucleotide at the end of each initiator. The array is rigid or semi-rigid and may be made out of silicon dioxide, glass, an insoluble polymer, or other material. The array has at least one substantially flat surface. The initiators may be attached to the array using any known technique for anchoring single-stranded DNA or RNA to a solid support such as techniques used in conventional solid-phase synthesis of oligonucleotides or used for creation of DNA microarrays.

Each of the initiators may be identical having the same length and nucleotide sequence. However, there may also be variation among the initiators in terms of length as well as sequence. In some implementations, the sequences of the initiators may include a cut site for restriction enzymes or other nucleases to cleave synthesized polynucleotides from the surface of the array. In some implementation, the initiators may serve as primer binding sites for subsequent amplification of the synthesized polynucleotides.

At 304, the array is incubated with a reaction reagent solution. The reaction reagent solution may be delivered to a reaction chamber that contains the array. The reaction reagent solution may be added to the reaction chamber by a manual technique such as pipetting. The reaction reagent solution may be added to the reaction chamber by an automated or mechanized system such as via a fluid delivery pathway. The reaction reagent solution includes a substrate independent polymerase such as TdT and a selected nucleotide.

In one implementation, the selected nucleotide is provided as a nucleotide mixture. The nucleotide mixture includes the selected nucleotide attached to a protecting group and unprotected forms of the selected nucleotide. The nucleotide mixture may be one of the nucleotide mixtures 218 shown in FIG. 2. In one implementation, only unprotected nucleotides are included in the reaction reagent solution. For example, the selected nucleotide may be one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP).

Incubation continues for a length of time referred to as a reaction time. The reaction time may be any length of time sufficient for polymerization to occur. If activity of the template independent polymerase is not stopped, such as by addition of nucleotides with protecting groups, increased reaction time increases the extension length. For example, the reaction time may be 10, 20, 30, 40, 50 seconds, 1, 2, 3, 4, 5, 10, 15, 20, 25, 30, 35, 40, 45, 50, 55, 60 minutes, or longer.

Incubation is performed at a reaction temperature. The reaction temperature may be maintained by a heater or heating element in the oligonucleotide synthesizer. The reaction temperature may be a temperature at which the template independent polymerase is active. The reaction temperature may be different for different polymerases. Further, changes in the reaction temperature may affect the extension length. Within the range of acceptable temperatures for a given polymerase, increases in reaction temperature generally increase the extension length. The reaction temperature may be, for example, between 20 and 40° C., such as 25, 30, or 37° C.

During the incubation, the template independent polymerase adds a variable number of nucleotides to the 3' end of the initiators. The variable number of nucleotides is the extension length obtained under a given set of reaction conditions. A target value for the variable number of nucleotides may be predetermined prior to the incubation at 304. For example, the target value for the variable number of nucleotides may be specified as part of an encoding scheme implemented by the encoding module 212 and the reaction conditions may be selected to achieve an average extension length that is the target value.

Reaction conditions that affect the variable number of nucleotides include the reaction time, the reaction temperature, the concentration of the template independent polymerase, and the concentration of free nucleotides. The density or number of initiators, specifically a number of available 3' ends, also affects the variable number of nucleotides because this controls the number of available reaction positions for a given concentration of polymerase and nucleotides. The concentration of the template independent polymerase may be measured in terms of enzyme activity which is represented in "units." One unit is defined as the amount of enzyme catalyzing the incorporation of 1 nmol dTTP into acid-insoluble material in a total reaction volume of 50 μl in 60 minutes at 37° C. using $d(A)_{18}$ (i.e., a single-stranded 18-mer of deoxyadenosine nucleoside) as an initiator. Persons of ordinary skill in the art will be able to tune the variable number of nucleotides based on adjusting these reaction conditions.

If the nucleotide mixture includes protected nucleotides, the ratio of unprotected nucleotides to protected nucleotides also affects the variable number of nucleotides. The variable number increases as a relative ratio of protected nucleotides decreases. For example, with a reaction time of one minute and a reaction temperature of 37° C. using 20 units of TDT for each 10 pmol of initiators, the variable number of nucleotides is about five with a 1:1 ratio of 0.25 mmol of dNTPs with protecting groups to 0.25 mmol of unprotected dNTPs.

If the selected nucleotide is provided only in unprotected form, then a ratio of the template independent polymerase (as measured in units) to the number of available 3' ends on the initiators, to the selected nucleotide affects the variable number of nucleotides. Holding other factors constant, the following examples show how adjusting the reaction time can affect the variable number of nucleotides.

At a reaction temperature of 37° C. using 20 units of TDT for each 10 pmol of initiators and 0.5 mmol of the selected nucleotide (without protecting groups), the variable number of nucleotides is about 10 for a reaction time of one minute. Under the same conditions, the variable number of nucleotides increases to about 40 for a reaction time of five minutes. As a further example, with a reaction time of 10 seconds and a reaction temperature of 25° C. using 10 units of TdT for each 10 pmol of initiators and 0.5 mmol of the selected nucleotide (without protecting groups), the variable number of nucleotides is about five.

At 306, process 300 branches depending on if protecting groups are present on at least some of the nucleotides incubated with the array. Process 300 proceeds along the "yes" path to 308 if protecting groups such as the protecting group 108 shown in FIG. 1 are present on the nucleotides. If not, process 300 proceeds along the "no" path to 316.

At 308, activity of the template independent polymerase is stopped at the end of the reaction time. The length of time until activity of the template independent polymerase is stopped may define the reaction time. Some ways to stop activity of the template independent polymerase include changing the oxidation state of a metal cofactor to an oxidation state other than +2 or removing access to the metal cofactor by chelation.

Other ways to stop activity of the template independent polymerase include inactivating the template independent polymerase through heating or denaturation with a surfactant. Preventing the nucleotides from polymerizing by cleaving the phosphate group can also prevent polymerization by denying the template independent polymerase reactive monomers. Another way of stopping activity of the template independent polymerase is to remove the template independent polymerase or the free nucleotides from contact with the surface of the array.

At 310, a wash solution is delivered to the array to remove the reaction reagent solution. The wash solution may be flowed across the entire reaction site displacing the reaction reagent solution and thereby stopping polymerization. Thus, in some implementations, operations 308 and 310 are the same because delivering the wash solution stops the activity of the template independent polymerase. The wash solution is water without added salts or an aqueous solution that contains at least one of a salt or a buffer. The buffer may be any one of a number of aqueous buffers that are compatible with polymerases and single-stranded nucleotides such as PBS or tris-buffered saline (TBS).

The wash solution also clears any remaining nucleotides from the previous cycle of synthesis from the reaction chamber and the surface of the array. This prevents incorporation of an incorrect nucleotide during a subsequent cycle of synthesis.

At 312, the protecting groups are removed from a selected location on the array. The protecting groups may be any kind of moiety or chemical group incorporated into the protected nucleotides. Some examples of protecting groups are esters, ethers, carbonitriles, phosphates, carbonates, carbamates, hydroxylamine, borates, nitrates, sugars, phosphoramides, phosphoramidates, phenylsulfenates, sulfates, sulfones, and amino acids.

The selected location on the array may be one or more spots that each contain multiple individual polynucleotides such as the spots 102 illustrated in FIG. 1. The selected location may be selected based on which polynucleotides are identified as receiving the next free nucleotide according to instructions such as instructions provided by the oligonucleotide synthesizer control module 206. The selected location may be changed one or more times during the synthesis of polynucleotides on the array.

The protecting groups are removed using a technique suitable for the type of protecting group such as by light, heat, electrochemistry, or pH. The spatially addressable deblocking through removal of the protecting groups may be implemented by use of a spatially addressable microelectrode array, a spatially addressable inkjet printing system, a spatially addressable light array, or another device.

At 314, it is determined if the polynucleotides are formed. If all nucleotides needed to create the specified sequence of the polynucleotides have been added, then the polynucleotides are fully formed. Process 300 may then proceed along the "yes" path and end or proceed to 324 and add a primer binding site to the 3' end of the fully-formed polynucleotide.

If, however, the polynucleotides are not yet fully formed, process 300 proceeds along "no" path and returns to 304 where the array is again incubated with a reaction reagent solution. The reaction reagent solution in this iteration of synthesis may include a different selected nucleotide. The subsequent iteration may also add the selected nucleotide to a different set of polynucleotides on the array by changing the selected location at which the protecting groups are removed.

At 316, if protecting groups are not used, polymerization is activated at a selected location on the array. Activating polymerization may be achieved by any technique that has a localized effect on the presence of specific components or reaction conditions that promote the activity of the template independent polymerase. In one implementation, the oxidation state of a metal cofactor of the template independent polymerase may be changed to a +2 oxidation state at the selected location thereby activating the polymerase. In one implementation, protecting groups attached to the template independent polymerase may be removed at the selected location thereby activating the polymerase. In one implementation, the selected nucleotide may be added only at the selected location.

Activating polymerization at the selected location on the array may also be achieved by globally activating polymerization across the array while inhibiting polymerization at locations on the array other than the selected location. One technique for inhibiting polymerization is physically blocking the template independent polymerase and/or the selected nucleotide from accessing locations on the array other than the selected location.

Access to locations on the array may be blocked by precise application of a fluid that does not contain the template independent polymerase or the selected nucleotide to the surface of the array. This will displace or dilute the template independent polymerase and/or the selected nucleotide at those locations thereby preventing polymerization. Another technique for physically blocking the template independent polymerase and/or the selected nucleotide is to deposit or create gas bubbles on the surface of the array. The gas bubbles prevent the reaction reagent solution containing the template independent polymerase and the selected nucleotide from contacting the array.

The selected location may be selected based on which polynucleotides are identified as receiving the next free nucleotide according to instructions such as instructions provided by the oligonucleotide synthesizer control module 206. The selected location may be changed one or more times during the synthesis of polynucleotides on the array.

At 318, activity of the template independent polymerase is stopped at the end of the reaction time. The length of time until the activity of the template independent polymerase is stopped may define the reaction time. Some ways to stop activity of the template independent polymerase include changing the oxidation state of a metal cofactor and removing access to the metal cofactor such as by chelation.

Additional ways include inactivating the template independent polymerase through heating or denaturation with a surfactant. Preventing the nucleotides from polymerizing by cleaving the phosphate group can also stop the activity of the template independent polymerase by denying it reactive monomers. Another way of stopping the activity of the template independent polymerase is to remove the template independent polymerase or the free nucleotides from contact with the surface of the array.

At 320, a wash solution is delivered to the array to remove the reaction reagent solution. The wash solution may be flowed across the entire reaction site displacing the reaction reagent solution and thereby stopping polymerization. Thus, in some implementations, operations 318 and 320 are the same because delivering the wash solution stops the activity of the template independent polymerase. The wash solution is water without added salts or an aqueous solution that contains at least one of a salt or a buffer. The buffer may be any one of a number of aqueous buffers that are compatible with polymerases and single-stranded nucleotides such as PBS or TBS.

The wash solution also clears any remaining nucleotides from the previous cycle of synthesis from the reaction chamber and the surface of the array. This prevents incorporation of an incorrect nucleotide during a subsequent cycle of synthesis.

At 322, it is determined if the polynucleotides are formed. If all nucleotides needed to create the specified sequence of the polynucleotides have been added, then the polynucleotides are fully formed. Process 300 may then proceed along the "yes" path and end or proceed to 324 and add a primer binding site to the 3' end of the fully-formed polynucleotide. If, however, the polynucleotides are not yet fully formed, process 300 proceeds along "no" path and returns to 304 where a reaction reagent solution is delivered to the reaction site. The reaction reagent solution in this subsequent iteration of synthesis may include a different selected nucleotide. A subsequent iteration may add nucleotides to a different set of polynucleotides on the array by changing the selected location used at 316.

At 324, a primer sequence may be added to the 3' ends of the fully-formed polynucleotides. The primer sequence may be added to the 3' end of a polynucleotide attached to an array by continuing enzymatic synthesis using a nucleotide mixture that contains only protected nucleotides. This restricts addition per round of synthesis to only one nucleotide for all or most of the polynucleotides. This precisely controlled addition allows for base-by-base control in creation of a specific sequence for the primer binding site.

Alternatively, the single-stranded nucleotide that will function as a primer binding site may be synthesized elsewhere (e.g., using the phosphoramidite method) and ligated onto the 3' end of the polynucleotide while still attached to the array. Techniques for ligation such as use of T4 DNA ligase are well-known to those of ordinary skill in the art.

Data Encoding with Enzymatically Synthesized Oligonucleotides

Figure 4:
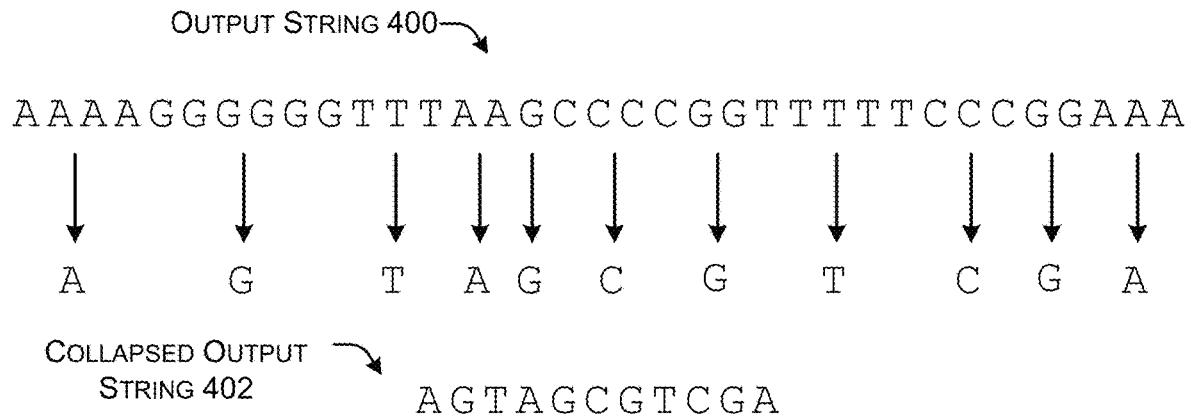
FIG. 4 shows an example decoding technique that converts output strings with homopolymers to collapsed sequence strings that have the homopolymers replaced with a lesser number of nucleotides.
Figure 4:
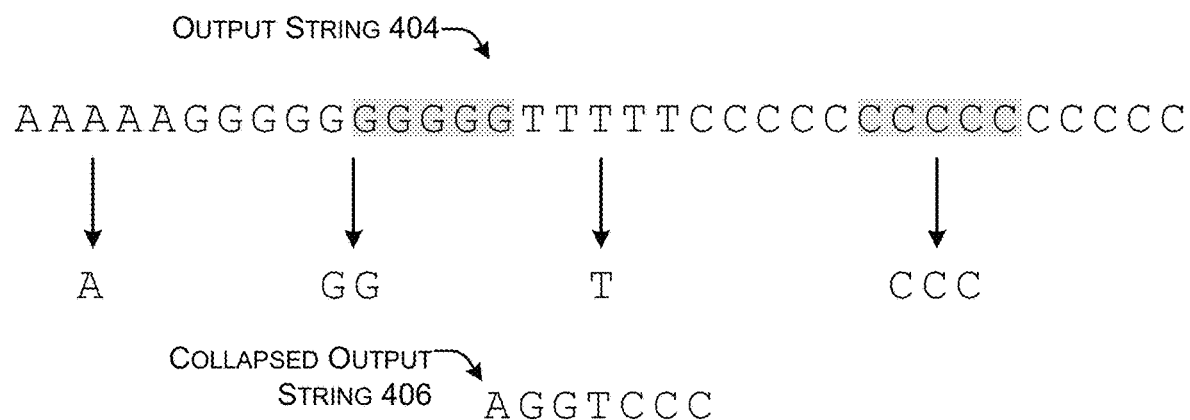

FIG. 4 illustrates encoding schemes for representing digital information as a sequence of nucleotides created by a template independent polymerase. The encoding scheme is tied to the behavior of template independent polymerases such as TdT because these polymerases add free nucleotides in an uncontrolled manner that creates homopolymers of variable length in the final polynucleotide. This variable length, also referred to as extension length, is not known in advance and is not uniform. The average extension length can be controlled to some extent with the techniques described above. However, even in a population of polynucleotides that are intended to have the same sequence (i.e., polynucleotides attached to a same spot on the surface of an array) there are variations in the extension length.

Encoding schemes for representing digital information in a sequence of nucleotides and for decoding and recovering digital information from a polynucleotide created with enzymatic synthesis do not depend on the technique used to synthesize the polynucleotide. That is to say, encoding schemes disclosed herein are equally applicable to enzymatically synthesized polynucleotides created on an addressable array or on a different type of solid support such as beads in a test tube.

The encoding of digital information in a sequence of nucleotides may be done according to an encoding scheme that excludes or that permits homopolymers in a nucleotide sequence string. As used herein, the term "string" indicates a representation of the order of nucleotides in a polynucleotide and not an actual DNA or RNA molecule. A nucleotide sequence string, for example, may be represented as a series of letters (e.g., A, G, C, T) in an electronic file such as FASTA file. Examples of encoding schemes for recording digital information in nucleotides that can be modified according to the teachings of this disclosure are known to those of ordinary skill in the art.

The encoding scheme may be implemented by an encoding module in a computing device such as encoding module 212 introduced in FIG. 2. If the encoding scheme excludes homopolymers, then the nucleotide sequence string that is generated will not have any repeats of the same nucleotide. It homopolymers are permitted, the length of homopolymers may be limited or bounded. For example, the encoding scheme may permit bounded homopolymers up to three repeats of the same nucleotide. Inclusion of homopolymers and increasing length of permissible bounded homopolymers both increase information density. Thus, a larger number of bits of digital information may be represented in the same length of polynucleotide if the encoding scheme accommodates homopolymers.

Regardless of whether the encoding scheme permits homopolymers, polynucleotides synthesized by a template independent polymerase include homopolymers. Thus, an output string created by sequencing these homopolymers with a polynucleotide sequencer will include homopolymers. The output string, like the nucleotide sequence string, is a representation of nucleotides in a polynucleotide. The output string reflects the order of individual nucleotide bases detected by a polynucleotide sequencer. The output string may be provided in an electronic file such as a FASTQ file.

With an encoding scheme that does not use homopolymers, an output string 400 (SEQ ID NO:1) is converted to a collapsed output string 402 (SEQ ID NO:2) by "collapsing" homopolymers in the output string 400 to single nucleotides. Thus, the start of the output string 400 AAAA is collapsed to a single A in the collapsed output string 402. The length of a homopolymer in the output string 400 does not affect the result. Every homopolymer regardless of length is collapsed to a single nucleotide. Portions of the output string 400 that do not include homopolymers are not changed by this operation.

With an encoding scheme that permits homopolymers, the length of the homopolymer is used to determine how to collapse an output string 404 (SEQ ID NO:3). As described above, the extension length may be controlled at least approximately by controlling and tuning reaction conditions. If, for example, the extension length is five nucleotides, then each single nucleotide in the nucleotide sequence string is represented by, approximately, five nucleotides in the output string 404. Thus, a 2-nucleotide homopolymer in the nucleotide sequence string will result in a homopolymer of approximate length 10 in the output string 404.

The output string 404 in this example includes a 10-nucleotide long homopolymer of Gs and a 15-nucleotide long homopolymer of Cs. These homopolymers are collapsed, respectively to a 2-nucleotide homopolymer of G and a 3-nucleotide homopolymer of C. Thus, the collapsed output string 406 includes shorter homopolymers than the output string 404. The lengths of the shorter homopolymers are based on the length of the homopolymers in the output string 404.

The lengths of the homopolymers in the output string 404 are not always precise multiples of the extension length. Thus, the length of homopolymers in the output string 404 may be rounded down or up to determining the length of homopolymer to include in the collapsed output string 406. The cutoff may be the midpoint between one extension length and the next. For example, if the extension length is five nucleotides, then any homopolymer of length 5-7 will be collapsed to a single nucleotide and any homopolymer of length 8-12 will be collapsed to a two-nucleotide homopolymer.

If the extension length is an even number, there may be homopolymers in the output string 404 with lengths that are exactly at the midpoint between one extension length and the next. For example, if the extension length is four, a homopolymer in the output string 404 of length six is equally likely to represent a single nucleotide or a two-nucleotide homopolymer. In this case, the number of nucleotides to include in the collapsed output string 406 may be decided by random selection. Alternatively, output strings 404 that include homopolymers of a length that is the midpoint between two integer multiples of the extension length may be discarded and not used for decoding the digital information.

Figure 5:
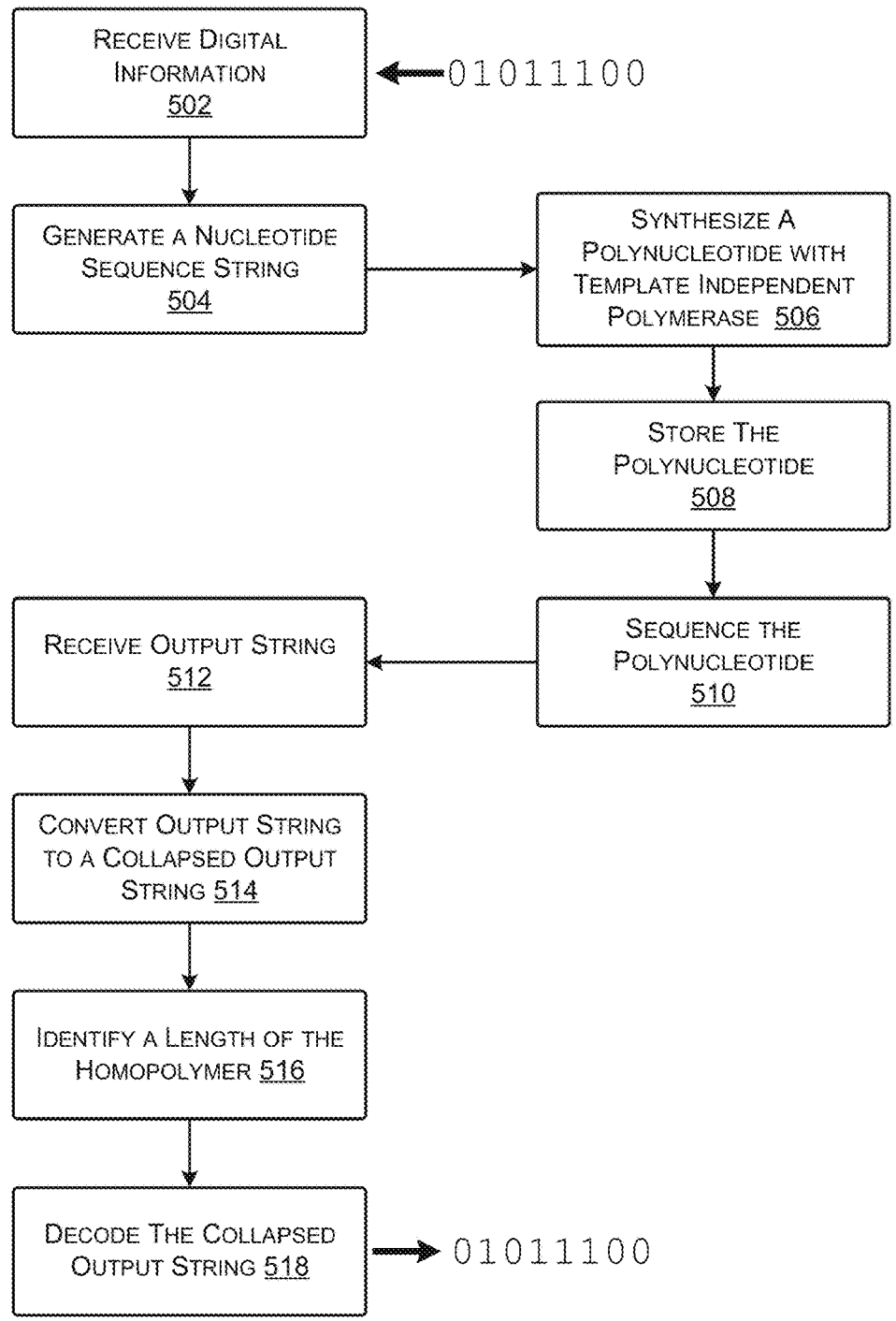
FIG. 5 is a flow diagram showing an illustrative process for using a template independent polymerase to synthesize a polynucleotide that encodes digital information and recovering the digital information by analyzing an output string generated from sequencing the polynucleotide.

FIG. 5 shows process 500 for storing digital information on polynucleotides synthesized with a template independent polymerase. This process 500 may be implemented, for example, using any of the reactions, structures, and devices shown in FIGS. 1 and 2 as well as the decoding scheme shown in FIG. 4. Process 500 includes some operations that are implemented on a computer through electronic processing and some operations that implemented through physical processing of nucleotides and polynucleotides.

At 502, digital information is received. The digital information may be a string of zeros and ones representing binary code for a computer file. For example, the digital information may be the same as the digital information 202 shown in FIG. 2.

At 504, the nucleotide sequence string is generated based on the digital information using an encoding scheme. The encoding scheme represents the digital information as a sequence of nucleotides. The encoding scheme may exclude or permit homopolymers in the nucleotide sequence string.

At 506, a polynucleotide including the digital information is synthesized according to the nucleotide sequence string with a template independent polymerase. The polynucleotide may be synthesized by an oligonucleotide synthesizer such as the oligonucleotide synthesizer 208 shown in FIG. 2. However, other devices and techniques for synthesizing the polynucleotide using a template independent polymerase are also suitable. Because the polynucleotide is synthesized with a template independent polymerase that adds multiple instances of the same nucleotide during a single synthesis cycle, the polynucleotide includes a homopolymer that is not present in the nucleotide sequence string.

At 508, the polynucleotide may be stored. The polynucleotide may be stored for a relatively short time in an aqueous solution such as the solution in which it was synthesized. The polynucleotide may be stored for a relatively longer period of time as a lyophilized pellet, encased in a protective coating, dried onto filter paper, or by another technique that preserves the structure of the polynucleotide. The polynucleotide, because it encodes digital information, represents a form of data storage.

At 510, polynucleotide including the digital information is sequenced. The polynucleotide may be sequenced with any type of sequencing technology such as the polynucleotide sequencer 222 shown in FIG. 2. Sequencing the polynucleotide generates an output string which represents the order of nucleotide bases as detected by the polynucleotide sequencer.

At 512, the output string is received. The output string may be received, for example, by the encoding module in a computing device such as encoding module 212 shown in FIG. 2. The output string may be received as an electronic file containing a sequence of letters or other symbols representing nucleotide bases. The output string, because it is a representation of the polynucleotide, also includes the homopolymer that is not present in the nucleotide sequence string. Thus, the output string from the polynucleotide sequencer does not match the input string provided to the oligonucleotide synthesizer.

At 514, the output string is converted to a collapsed output string. The output string is converted to the collapsed output string by replacing the homopolymer in the output string with fewer nucleotides. If the encoding scheme used to generate the nucleotide sequence string excludes homopolymers, then the fewer nucleotides is a single nucleotide. Thus, any homopolymer sequence in the output string is collapsed to a single nucleotide. An example of converting an output string that is encoded without homopolymers is shown by the output string 400 and the collapsed output string 402 of FIG. 4.

If the encoding scheme used to generate the nucleotide sequence string allows homopolymers, then the fewer number of nucleotides is based on a length of the homopolymer in the output string. Thus, the fewer number of nucleotides may be a single nucleotide or it may be a homopolymer such as a string of the same nucleotide repeated two or three times. The fewer number of nucleotides may be further based on a variable number of nucleotides added by the template independent polymerase during a single synthesis cycle. As described above, this variable number of nucleotides may be adjusted at least approximately by controlling the reaction conditions of the synthesis. An example of converting an output string that is encoded with homopolymers is shown by the output string 404 and the collapsed output string 406 of FIG. 4.

At 516, the length of the homopolymer in the output string is identified. The number of nucleotides in the output string that form any given homopolymer can be counted and recorded. This resulting number of nucleotides in the converted output string may also be identified and the change in the number of nucleotides for the homopolymer can thus be identified and recorded. For example, collapsing a string of TTTT to T may be identified as a 4:1 change in the number of nucleotides. As an additional example, collapsing a string of GGGGGG to GG may be identified as a 6:2 change.

At 518, the collapsed output string is decoded using the encoding scheme to recover the digital information. The technique for decoding the collapsed output string may use the length of the homopolymer identified at 516 as one piece of information about the output string that is processed by a decoding pipeline. The decoding may be performed by the encoding module 212 or by an encoding and/or decoding module on another computing device besides the computing device 204 that provided the nucleotide sequence string.

Illustrative Computer Architecture

Figure 6:
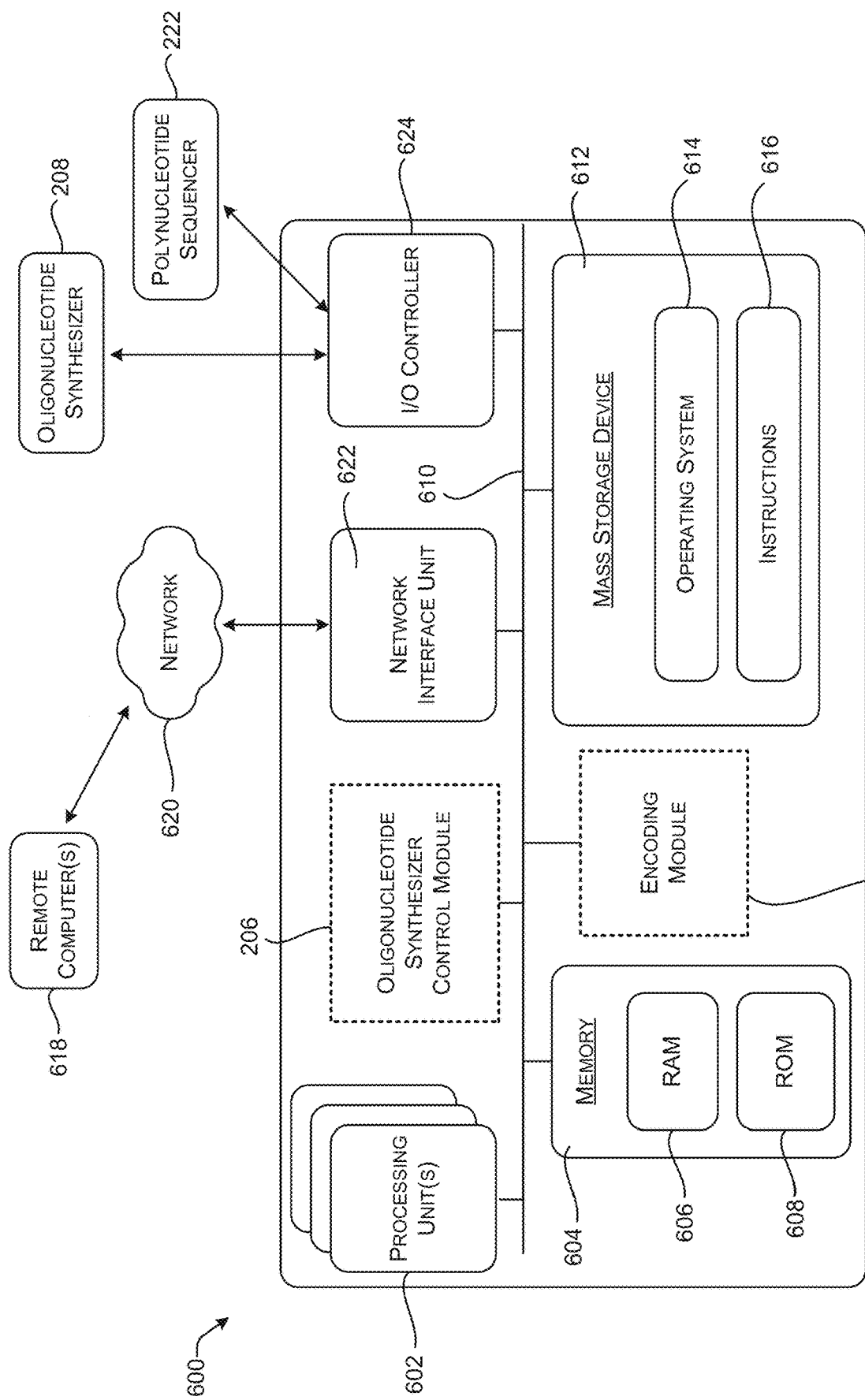
FIG. 6 is an illustrative computer architecture for implementing techniques of this disclosure.

FIG. 6 is a computer architecture diagram showing an illustrative computer hardware and software architecture for a computing device such as the computing device 204 introduced FIG. 2. In particular, the computer 600 illustrated in FIG. 6 can be utilized to implement the oligonucleotide synthesizer control module 206 or the encoding module 212 introduced in FIG. 2.

The computer 600 includes one or more processing units 602, a memory 604, that may include a random-access memory 606 ("RAM") and a read-only memory ("ROM") 608, and a system bus 610 that couples the memory 604 to the processing unit(s) 602. A basic input/output system ("BIOS" or "firmware") containing the basic routines that help to transfer information between elements within the computer 600, such as during startup, can be stored in the ROM 608. The computer 600 further includes a mass storage device 612 for storing an operating system 614 and other instructions 616 that represent application programs and/or other types of programs such as, for example, instructions to implement the oligonucleotide synthesizer control module 206. The mass storage device 612 can also be configured to store files, documents, and data such as, for example, sequence data that is provided to an oligonucleotide synthesizer 208 in the form of instructions.

The mass storage device 612 is connected to the processing unit(s) 602 through a mass storage controller (not shown) connected to the bus 610. The mass storage device 612 and its associated computer-readable media provide non-volatile storage for the computer 600. Although the description of computer-readable media contained herein refers to a mass storage device, such as a hard disk, solid-state drive, CD-ROM drive, DVD-ROM drive, or USB storage key, it should be appreciated by those skilled in the art that computer-readable media can be any available computer-readable storage media or communication media that can be accessed by the computer 600.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules or other data. For example, computer-readable storage media includes, but is not limited to, RAM 606, ROM 608, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 600. For purposes of the claims, the phrase "computer-readable storage medium," and variations thereof, does not include waves or signals per se or communication media.

According to various configurations, the computer 600 can operate in a networked environment using logical connections to a remote computer(s) 618 through a network 620. The computer 600 can connect to the network 620 through a network interface unit 622 connected to the bus 610. It should be appreciated that the network interface unit 622 can also be utilized to connect to other types of networks and remote computer systems. The computer 600 can also include an input/output (I/O) controller 624 for receiving and processing input from a number of other devices, including a keyboard, mouse, touch input, an electronic stylus (not shown), or equipment such as an oligonucleotide synthesizer 208 and/or a polynucleotide sequencer 222. Similarly, the input/output controller 624 can provide output to a display screen or other type of output device (not shown).

It should be appreciated that the software components described herein, when loaded into the processing unit(s) 602 and executed, can transform the processing unit(s) 602 and the overall computer 600 from a general-purpose computing device into a special-purpose computing device customized to facilitate the functionality presented herein. The processing unit(s) 602 can be constructed from any number of transistors or other discrete circuit elements, which can individually or collectively assume any number of states. More specifically, the processing unit(s) 602 can operate as a finite-state machine, in response to executable instructions contained within the software modules disclosed herein. These computer-executable instructions can transform the processing unit(s) 602 by specifying how the processing unit(s) 602 transitions between states, thereby transforming the transistors or other discrete hardware elements constituting the processing unit(s) 602.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 600 to store and execute the software components presented herein. It also should be appreciated that the architecture shown in FIG. 6 for the computer 600, or a similar architecture, can be utilized to implement many types of computing devices such as desktop computers, notebook computers, servers, supercomputers, gaming devices, tablet computers, and other types of computing devices known to those skilled in the art. For example, the computer 600 may be wholly or partially integrated into the oligonucleotide synthesizer 208. It is also contemplated that the computer 600 might not include all of the components shown in FIG. 6, can include other components that are not explicitly shown in FIG. 6, or can utilize an architecture different than that shown in FIG. 6.

ILLUSTRATIVE EMBODIMENTS

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1: A method for synthesizing multiple polynucleotides having different sequences using a template independent polymerase, the method comprising: (a) incubating an array covered with a plurality of initiators for a reaction time at a reaction temperature with a reaction reagent solution comprising the template independent polymerase and a nucleotide mixture of a selected nucleotide comprising unprotected nucleotides such that the template independent polymerase adds a variable number of nucleotides to 3'ends of the initiators, the variable number of nucleotides based on a ratio of the unprotected nucleotides to the protected nucleotides; (b) after the reaction time, stopping activity of the template independent polymerase; (c) delivering a wash solution to the array to remove the reaction reagent solution; (d) removing the protecting group from a selected location on the array; and (e) iteratively repeating steps (a), (b), (c), and (d) until the multiple polynucleotides are formed.

Clause 2: The method of clause 1, wherein during iterations of repeating steps (a), (b), (c), and (d) the selected nucleotide and the selected location both change at least once.

Clause 3: The method of any of clauses 1-2, wherein a target value for the variable number of nucleotides is predetermined prior to the incubating.

Clause 4: The method of any of clauses 1-3, wherein the template independent polymerase comprises TdT.

Clause 5: The method of any of clauses 1-4, wherein the selected nucleotide is one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP).

Clause 6: The method of any of clauses 1-5, wherein the protecting group is a chemical group incorporated into the protected nucleotides and is removable by light, heat, electrochemistry, or pH.

Clause 7: The method of any of clauses 1-6, wherein stopping the activity of the template independent polymerase comprises changing an oxidation state of a metal cofactor for the template independent polymerase to an oxidation state other than +2.

Clause 8: The method of any of clauses 1-7, further comprising adding a primer sequence with a specific base-by-base sequence on to 3' ends of the multiple polynucleotides.

Clause 9: A method of synthesis of multiple polynucleotides having different sequences using a template independent polymerase, the method comprising: (a) incubating an array covered with a plurality of initiators for a reaction time at a reaction temperature with a reaction reagent solution comprising the template independent polymerase and a selected nucleotide such that the template independent polymerase adds a variable number of nucleotides to 3' ends of the initiators, the variable number of nucleotides based on a ratio of the template independent polymerase to the initiators to the selected nucleotide; (b) activating polymerization at a selected location on the array; (c) after the reaction time, stopping activity of the template independent polymerase; (d) delivering a wash solution to the array to remove the reaction reagent solution; and (e) iteratively repeating steps (a), (b), (c), and (d) until the multiple polynucleotides are formed, wherein during iterations of repeating steps (a), (b), (c), and (d) the selected nucleotide and the selected location both change at least once.

Clause 10: The method of clause 9, wherein a target value for the variable number of nucleotides is predetermined prior to the incubating.

Clause 11: The method of any of clauses 9-10, wherein the activating the polymerization at the selected location comprises changing an oxidation state of a metal cofactor of the template independent polymerase at the selected location, removing a protecting group from the template independent polymerase at the selected location, or adding the selected nucleotide at the selected location.

Clause 12: The method of any of clauses 9-11, wherein the activating the polymerization at the selected location comprises inhibiting the polymerization at locations on the array other than the selected location by physically blocking the template independent polymerase, the selected nucleotide, or both from accessing the locations on the array other than the selected location during the incubating.

Clause 13: The method of any of clauses 9-12, wherein stopping activity of the template independent polymerase comprises heating the reaction reagent solution to at least 60° C., denaturing the template independent polymerase with a surfactant, adding a chelator to the reaction reagent solution, or changing an oxidation state of a metal cofactor for the template independent polymerase to an oxidation state other than +2.

Clause 14: A method of decoding digital information in a polynucleotide synthesized by a template independent polymerase comprising: receiving an output string from sequencing of the polynucleotide that encodes the digital information according to a nucleotide sequence string generated by an encoding scheme, wherein synthesis with the template independent polymerase causes the polynucleotide to include a homopolymer that is not present in the nucleotide sequence string; converting the output string to a collapsed output string by replacing the homopolymer in the output string with fewer nucleotides; and decoding the collapsed output string using the encoding scheme to recover the digital information.

Clause 15: The method of clause 14, wherein the nucleotide sequence string generated by the encoding scheme excludes homopolymers and the fewer nucleotides is a single nucleotide.

Clause 16: The method of clause 14, wherein the nucleotide sequence string generated by the encoding scheme includes homopolymers and a number of the fewer nucleotides is based on a length of the homopolymer.

Clause 17: The method of clause 16, wherein the number of the fewer nucleotides is further based on a variable number of nucleotides added by the template independent polymerase during a single synthesis cycle.

Clause 18: The method of any of clauses 14-17, further comprising identifying a length of the homopolymer in the output string, wherein decoding the collapsed output string is based on a number of nucleotides in the homopolymer.

Clause 19: The method of any of clauses 14-18, further comprising sequencing the polynucleotide encoding the digital information thereby generating the output string.

Clause 20: The method of any of clauses 14-19, further comprising: generating the nucleotide sequence string from the digital information using the encoding scheme; synthesizing the polynucleotide encoding the digital information according to the nucleotide sequence string with the template independent polymerase; and sequencing the polynucleotide encoding the digital information thereby generating the output string.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents, and/or patent applications throughout this specification. Each of the cited references is individually incorporated herein by reference for its particular cited teachings as well as for all that it discloses.

The invention claimed is:

1. A method for synthesizing multiple polynucleotides having different sequences using a template independent polymerase, the method comprising:
   (a) incubating an array covered with a plurality of initiators for a reaction time at a reaction temperature with a reaction reagent solution comprising the template independent polymerase and a nucleotide mixture comprising unprotected nucleotides and protected nucleotides both having a same base such that the template independent polymerase adds a variable number of nucleotides to 3'ends of the initiators, the variable number of nucleotides based on a ratio of the unprotected nucleotides to the protected nucleotides;
   (b) after the reaction time, stopping activity of the template independent polymerase;
   (c) delivering a wash solution to the array to remove the reaction reagent solution;
   (d) removing the protecting group from a selected location on the array; and
   (e) iteratively repeating steps (a), (b), (c), and (d) until the multiple polynucleotides are formed, wherein polymerization kinetics differs depending on a base attached to the nucleotides and the ratio of the unprotected nucleotides to the protected nucleotides is selected such that the variable number of nucleotides is the same for each base.

2. The method of claim 1, wherein during iterations of repeating steps (a), (b), (c), and (d) the nucleotide mixture and the selected location both change at least once.

3. The method of claim 1, wherein a target value for the variable number of nucleotides is predetermined prior to the incubating and further comprising:
   selecting the ratio of the unprotected nucleotides to the protected nucleotides to achieve an extension length that equals the target value.

4. The method of claim 1, wherein the template independent polymerase comprises terminal deoxynucleotidyl transferase (TdT).

5. The method of claim 1, wherein the unprotected nucleotide is one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP).

6. The method of claim 1, wherein the protecting group is a chemical group incorporated into the protected nucleotides and is removable by heat.

7. The method of claim 1, wherein stopping the activity of the template independent polymerase comprises changing an oxidation state of a metal cofactor for the template independent polymerase to an oxidation state other than +2.

8. The method of claim 1, further comprising adding a primer sequence with a specific base-by-base sequence on to 3' ends of the multiple polynucleotides.

9. The method of claim 1, wherein the selected location on the array is less than an entirety of the array.

10. The method of claim 1, wherein the protecting group is a chemical group incorporated into the protected nucleotides and is removable by light.

11. The method of claim 10, wherein removing the protecting group from a selected location on the array comprises activating a portion of a spatially addressable light array.

12. The method of claim 1, wherein the protecting group is a chemical group incorporated into the protected nucleotides and is removable by electrochemistry.

13. The method of claim 12, wherein the array is a microelectrode array and removing the protecting group from a selected location on the array comprises activating a portion of the microelectrode array.

14. The method of claim 1, wherein the protecting group is a chemical group incorporated into the protected nucleotides and is removable by pH.

15. The method of claim 14, wherein removing the protecting group from a selected location on the array comprises delivering a reagent to the selected location by a spatially addressable inkjet printing system.

* * * * *

SEQUENCE LISTING

```
<160> NUMBER OF SEQ ID NOS: 3

<210> SEQ ID NO 1
<211> LENGTH: 35
<212> TYPE: DNA
<213> ORGANISM: Artificial Sequence
<220> FEATURE:
<223> OTHER INFORMATION: for illustrative purposes

<400> SEQUENCE: 1
aaaagggggg tttaagcccc ggttttttccc ggaaa                        35
```

```
<210> SEQ ID NO 2
<211> LENGTH: 11
<212> TYPE: DNA
<213> ORGANISM: Artifical Sequence
<220> FEATURE:
<223> OTHER INFORMATION: for illustrative purposes

<400> SEQUENCE: 2
agtagcgtcg a                                                            11

<210> SEQ ID NO 3
<211> LENGTH: 35
<212> TYPE: DNA
<213> ORGANISM: Artificial Sequence
<220> FEATURE:
<223> OTHER INFORMATION: for illustrative purposes

<400> SEQUENCE: 3
aaaaaggggg gggggttttt cccccccccc ccccc                                  35
```